United States Patent
Goto et al.

(10) Patent No.: US 7,949,170 B2
(45) Date of Patent: May 24, 2011

(54) IMAGE PROCESSING METHOD, IMAGE PROCESSING DEVICE, COMPUTER AIDED DETECTION, AND METHOD FOR FILTERING ALONG THE TIME AXIS

(75) Inventors: Taiga Goto, Kashiwa (JP); Osamu Miyazaki, Moriya (JP); Koichi Hirokawa, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 1389 days.

(21) Appl. No.: 10/579,514

(22) PCT Filed: Nov. 8, 2004

(86) PCT No.: PCT/JP2004/016537
§ 371 (c)(1),
(2), (4) Date: May 12, 2006

(87) PCT Pub. No.: WO2005/046478
PCT Pub. Date: May 26, 2005

(65) Prior Publication Data
US 2007/0126730 A1 Jun. 7, 2007

(30) Foreign Application Priority Data
Nov. 12, 2003 (JP) ................................. 2003-382081

(51) Int. Cl.
*G06K 9/00* (2006.01)
(52) U.S. Cl. ........................................ 382/131; 382/132
(58) Field of Classification Search .................... None
See application file for complete search history.

(56) References Cited

U.S. PATENT DOCUMENTS
7,545,967 B1 * 6/2009 Prince et al. ............... 382/130

FOREIGN PATENT DOCUMENTS
| CN | 85101311 A | | 1/1987 |
|---|---|---|---|
| JP | 8-131414 | | 5/1996 |
| JP | 11-137552 | | 5/1999 |
| JP | 11137552 A | * | 5/1999 |
| JP | 2001-252263 | | 9/2001 |
| JP | 2003-179812 | | 6/2003 |

OTHER PUBLICATIONS

Machine English translation of JP 2001-252263, to Hitoshi, published Sep. 18, 2001, translation pp. 1-25.*
Machine Enghish tranlsation of JP 11-137552, to Yasuto et al., published May 25, 1999, translation pp. 1-8.*
International Preliminary Report on Patentability (PCT/JP2004/016537), 7 pages total.
Sep. 21, 2010 Japanese official action in connection with counterpart Japanese patent application.
Jun. 16, 2008 official action in connection with a counterpart Chinese patent application No. 2004-800334596 (and English translation thereof), 25 pages total.

* cited by examiner

*Primary Examiner* — Brian P Werner
(74) *Attorney, Agent, or Firm* — Cooper & Dunham, LLP

(57) ABSTRACT

An image processing method comprises: an inputting step of inputting image data which is obtained by imaging a subject for a predetermined period of time with a medical imaging apparatus and is arranged in time series; an extracting along the time axis step of extracting pixels which satisfy a predetermined condition along the time axis from all the pixels arranged in time series for each pixel coordinate position with respect to each pixel in the image data; and a constructing step of constructing a two-dimensional or three-dimensional image based on the pixels extracted along the time axis in the extracting along the time axis step.

15 Claims, 17 Drawing Sheets

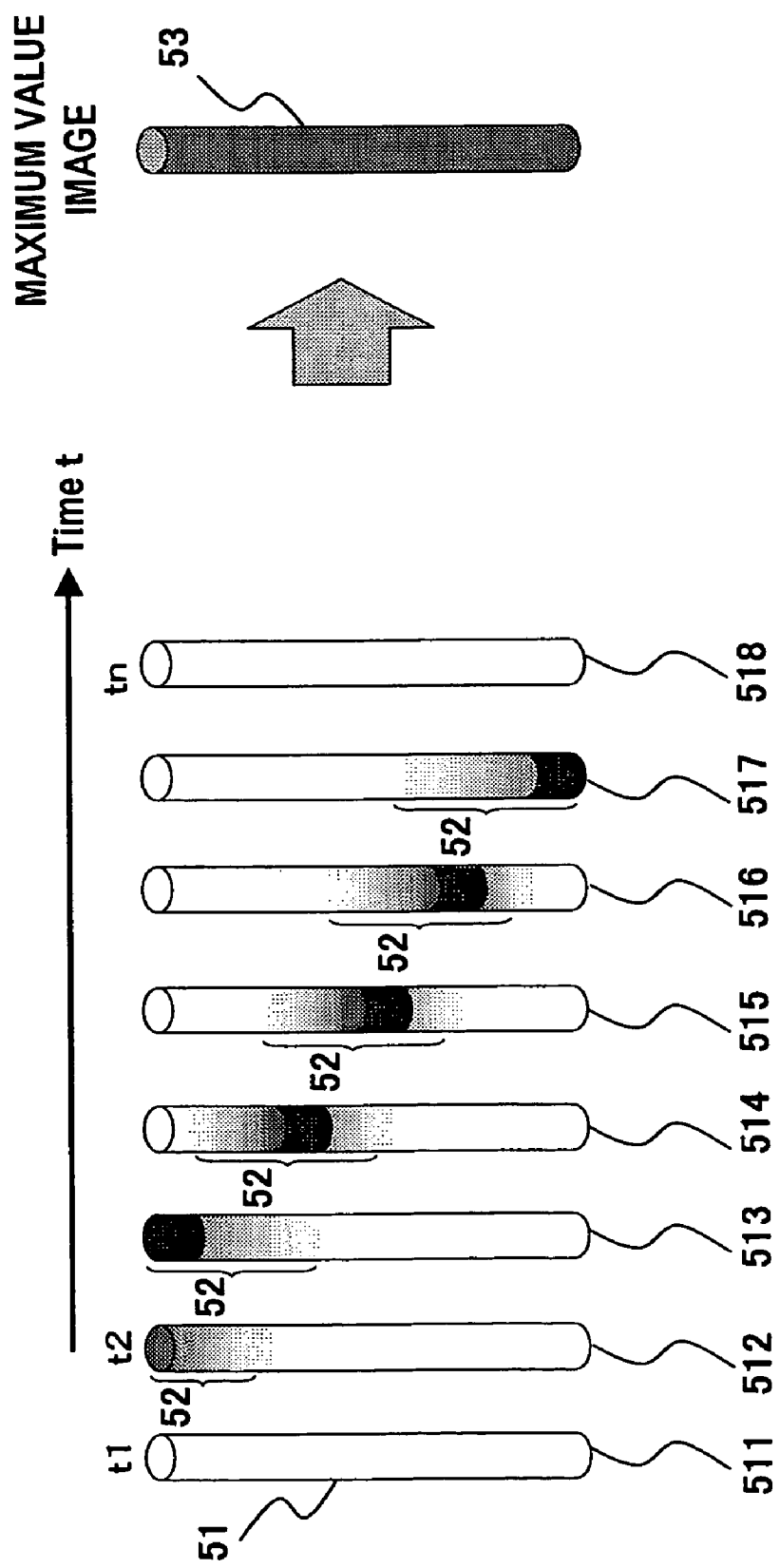

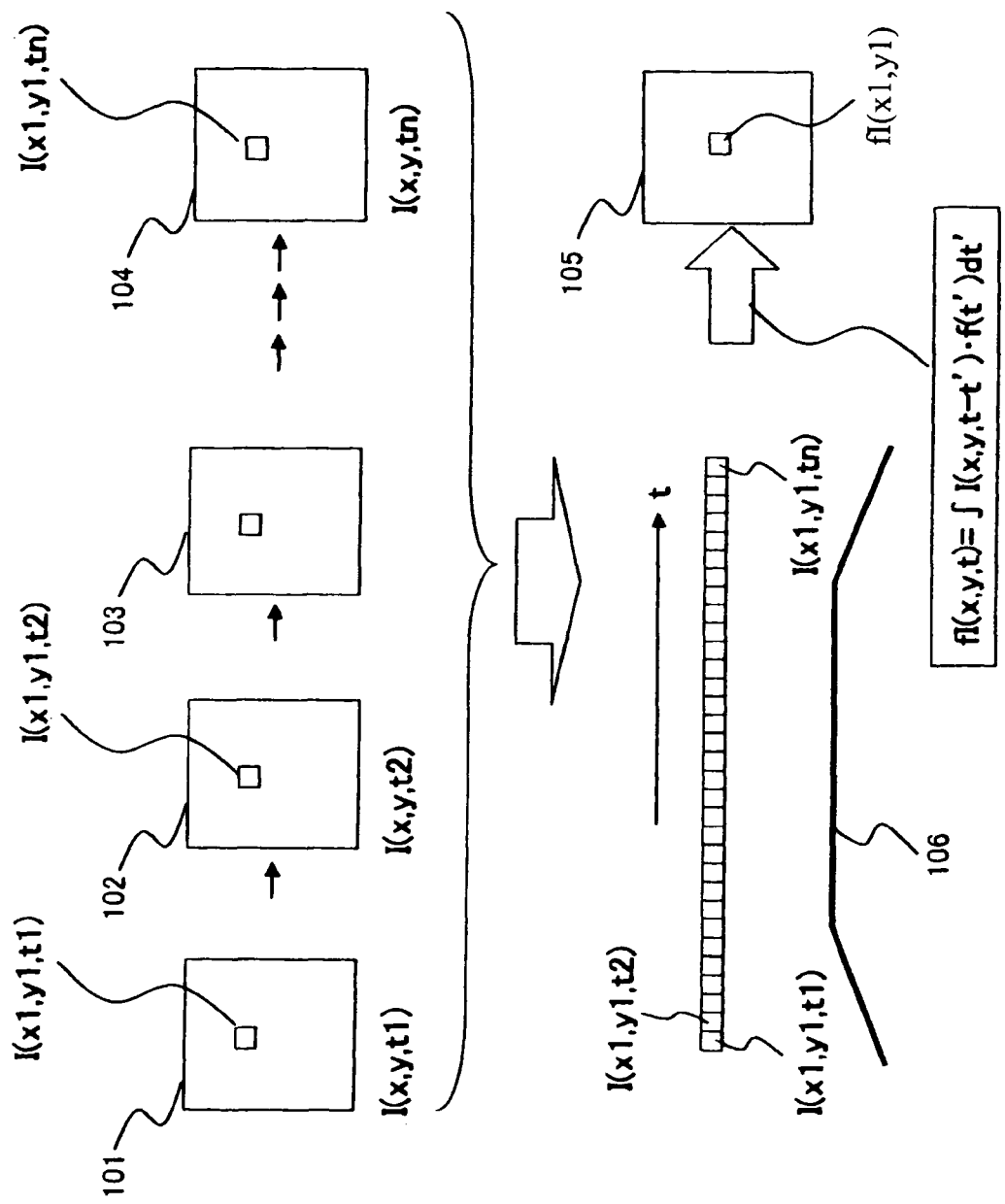

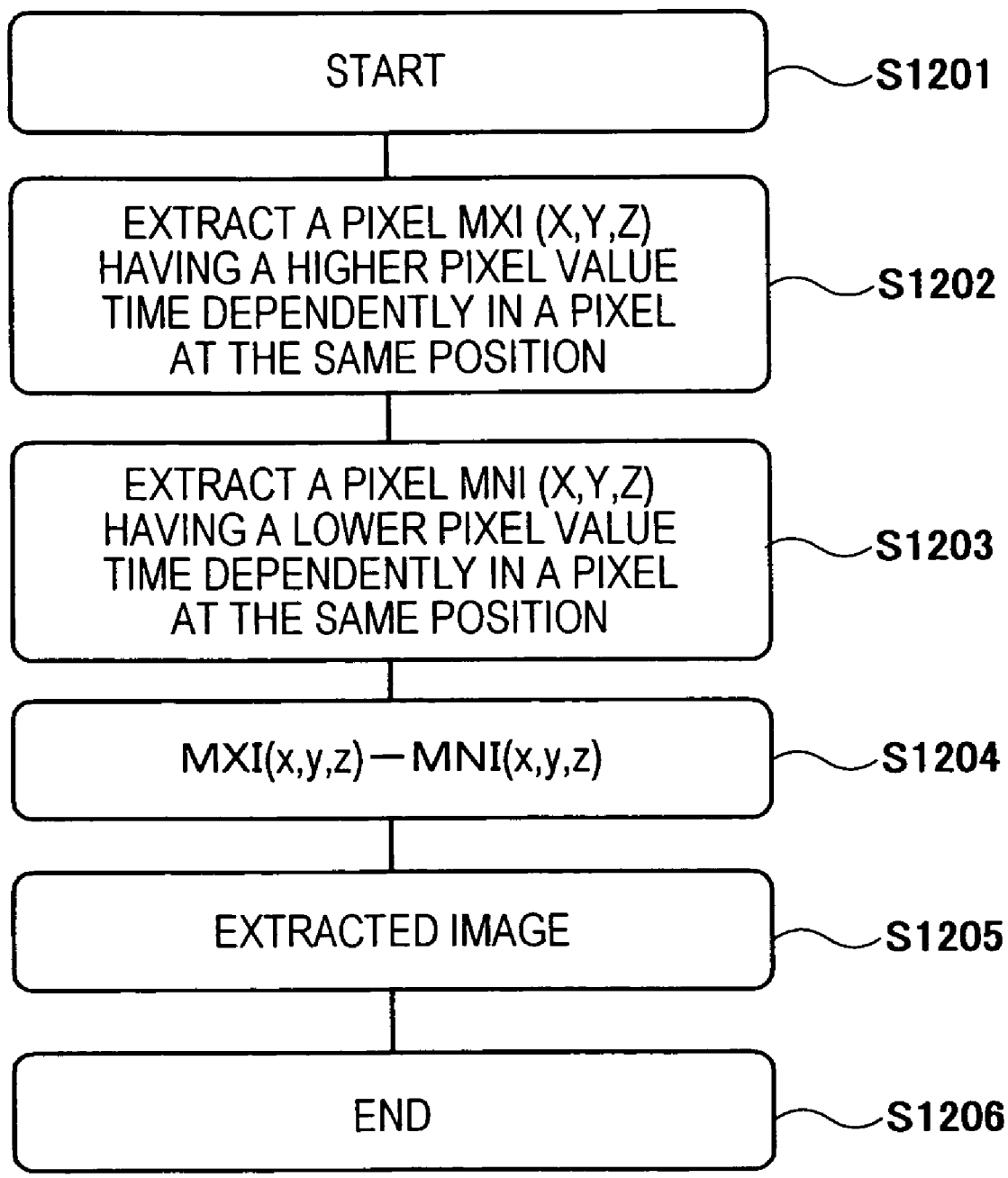

IMAGE PROCESSING METHOD, IMAGE PROCESSING DEVICE, COMPUTER AIDED DETECTION, AND METHOD FOR FILTERING ALONG THE TIME AXIS

TECHNICAL FIELD

The present invention relates to an image processing method, an image processing device, a computer aided detection (CAD), and a method for filtering along the time axis, and in particular, to an image processing method, an image processing device, a computer aided detection, and a method for filtering along the time axis which extract or rearrange pixels in image data for a specific display based on the image data obtained with a medical imaging apparatus such as an X-ray CT (Computed Tomography) apparatus, an MRI (Magnetic Resonance Imaging) apparatus, and a US (Ultrasound) imaging apparatus.

BACKGROUND ART

Angiography with a contrast medium is performed for example in an X-ray CT apparatus, an MRI apparatus, and a US apparatus.

The angiography with a contrast medium with an X-ray CT apparatus is called CTA (Computed Tomography Angiography), and the angiography with a contrast medium with an MRI apparatus is called MRA (Magnetic Resonance Imaging Angiography).

As an application of the angiography, Patent Document 1 discloses a method for displaying an angiographic image in which a state of contrast medium injection is displayed time dependently. This method uses Digital Subtraction Angiography (hereinafter, referred to as "DSA") to extract only the contrasted images of a blood vessel. DSA is a method to take images before and after the injection of a contrast medium and display a difference between the images. In the method for displaying angiographic images disclosed in the Patent Document 1, an image of a contrast medium which passes a certain cross section is acquired at predetermined periods of time by DSA, and the images of a contrast medium are arranged time dependently to display a time dependent transition of contrast medium images at the cross section. Since the images of a contrast medium display an amount of the contrast medium therein, a time dependent transition of the amount of the contrast medium at the cross section is provided.

However, in the above-described method for displaying angiographic images, the amount of a contrast medium at a cross section can be checked, but a special three-dimensional image of a contrasted blood vessel and the like cannot be displayed. [Patent Document 1] Japanese Patent Application Laid-Open No. 11-137552

BRIEF SUMMARY

In an aspect of this disclosure, there is provided an approach to display a desired image, for example an entire image of a contrasted blood vessel as a special three-dimensional image based on image data which is obtained in time series.

In another aspect of this disclosure, there is provided an approach to provide an image to display a contrasted blood vessel which does not have uneven results caused by an error in imaging timings or imaging locations or a concentration of a contrast medium in the blood vessel without changing the conventional amount of a contrast medium, and to prevent any increase of an amount of X-ray to which a subject is exposed by starting the imaging all over again.

In another aspect of this disclosure, there is provided an approach, in extracting a certain region, to reduce the time required for operation, and to eliminate a variation in accuracy in extracting a region caused by individual differences between operators.

In another aspect of this disclosure, there is provided a method, comprising: an inputting step of inputting an image data which is obtained by imaging a subject for a predetermined time with a medical imaging apparatus and is arranged in time series; an extracting along the time axis step of extracting pixels which satisfy a predetermined condition along the time axis from all the pixels arranged in time series for each pixel coordinate position, with respect to each pixel in the image data; and a constructing step of constructing a two-dimensional or three-dimensional image based on the pixels extracted along the time axis in the extracting along the time axis step.

The term "two-dimensional or three-dimensional image" used in the present invention is an image expressed in terms of the coordinate positions by using two coordinates or three coordinates.

A "two-dimensional image" in the present invention includes a cross section image which is acquired by imaging a certain cross section, as well as a two-dimensional projected image which is acquired by projecting three-dimensional image data obtained by imaging a subject.

Also, the term "extract a pixel" used in the present invention means to extract data to determine a pixel at a specific time in a predetermined period, and includes to extract a pixel coordinate position and a time coordinate to determine a pixel at a specific time, to extract only data which specify a time, or to extract a pixel value corresponding to a pixel at a specific time along the time axis, from all the pixels arranged in time series for each pixel coordinate position.

Also, the term "filtering along the time axis" used in the present invention means a process to perform a predetermined process to proved a predetermined effect along the time axis with respect to the image data or pixels arranged in time series, and the process includes an extraction along the time axis to extract pixels which satisfy a predetermined condition of such as the maximum value or the minimum value along the time axis from the image data arranged in time series, and a weighting along the time axis to weight image data arranged in time series along the time axis. The weighting along the time axis includes, for example, to assign a higher weight to image data taken at around the middle in a predetermined period of time for imaging, and to assign a lower weight to image data taken at the beginning and the end of the period of time for imaging.

In another aspect of this disclosure, there is provided an image processing method, comprising: an inputting step of inputting an image data which is obtained by imaging a subject into which a contrast medium is injected for a predetermined period of time with a medical imaging apparatus and is arranged in time series; an image reconstructing step of reconstructing three-dimensional images arranged in time series based on the image data; an extracting along the time axis step, with respect to each pixel constituting the three-dimensional image arranged in time series, of extracting a maximum value pixel which has a clearest contrasted image by the contrast medium and a minimum value pixel which has little or no residual contrast medium therein from all the pixels arranged in time series for each pixel coordinate position along the time axis; a constructing step of constructing a two-dimensional or three-dimensional image which has a clearest contrasted image by the contrast medium based on the maximum value pixel and a two-dimensional or three-dimensional image which has little or no residual contrast medium therein based on the minimum value pixel; a difference operation step of performing a difference operation on the two-dimensional or three-dimensional image which has a clearest contrasted image by the contrast medium and the two-dimensional or three-dimensional image which has little or no residual contrast medium therein; and a difference image producing step of producing a difference image based on the result of the difference operation.

In another aspect of this disclosure, there is provided an image processing method, comprising: an inputting step of inputting an image data which is obtained by imaging a subject for a predetermined time with a medical imaging apparatus and is arranged in time series; a filtering along the time axis step of performing a filtering process along the time axis on all the pixels arranged in time series for each pixel coordinate position and perform a predetermined weighting process along the time axis in time series with respect to each pixel in the image data; and a constructing step of constructing a two-dimensional or three-dimensional image based on the image data on which the filtering process along the time axis was performed by the filtering step along the time axis.

In another aspect of this disclosure, there is provided an mage processing method, comprising: an inputting step of inputting an image data which is obtained by imaging a subject for a predetermined period of time with a medical imaging apparatus and is arranged in time series; a calculating step of calculating the amount of change between the pixel value of each pixel in the image data at a first time in the predetermined period of time and the pixel value of each pixel in the image data at a second time in the predetermined period of time; a calculating step of calculating an average value of the pixel values from the first time to the second time for each pixel coordinate position, with respect to each pixel in the region where the amount of change is a predetermined value or less; and a producing step of producing a processed image in which the pixel value of each pixel in the region where the amount of change is the predetermined value or less has the average value and the pixel value of each pixel in the region where the amount of change is more than the predetermined value has the pixel value of the image data.

In another aspect of this disclosure there is provided an image processing device, comprising: an inputting means which inputs an image data obtained by imaging a subject for a predetermined period of time with a medical imaging apparatus and is arranged in time series; an extracting along the time axis means which extracts pixels satisfying a predetermined condition along the time axis from all the pixels arranged in time series for each pixel coordinate position, with respect to each pixel in the image data; and a constructing means which constructs a two-dimensional or three-dimensional image based on the pixels extracted along the time axis by the extracting along the time axis means.

In another aspect of this disclosure there is provided an image processing device, comprising: an inputting means which inputs an image data obtained by imaging a subject into which a contrast medium is injected for a predetermined period of time with a medical imaging apparatus and arranged in time series; an image reconstructing means which reconstructs three-dimensional images arranged in time series based on the image data; an extracting along the time axis means which extracts, with respect to each pixel constituting the three-dimensional image arranged in time series, a maximum value pixel which has a clearest contrasted image by the contrast medium and a minimum value pixel which has little or no residual contrast medium therein from all the pixels arranged in time series for each pixel coordinate position along the time axis; a constructing means which constructs a two-dimensional or three-dimensional image which has a clearest contrasted image by the contrast medium based on the maximum value pixel and a two-dimensional or three-dimensional image which has little or no residual contrast medium therein based on the minimum value pixel; a difference operation means which performs a difference operation on the two-dimensional or three-dimensional image which has a clearest contrasted image by the contrast medium and the two-dimensional or three-dimensional image which has little or no residual contrast medium therein; and a difference image producing means which produces a difference image based on the result of the difference operation.

In another aspect of this disclosure, there is provided an image processing device, comprising: an inputting means which inputs an image data obtained by imaging a subject for a predetermined period of time with a medical imaging apparatus and is arranged in time series; a filtering along the time axis means which performs a filtering process along the time axis on all the pixels arranged in time series for each pixel coordinate position and perform a predetermined weighting along the time axis along the time series, with respect to each pixel in the image data; and a constructing means to construct a two-dimensional or three-dimensional image based on the image data on which the filtering process along the time axis was performed by the filtering step along the time axis means.

In another aspect of this disclosure, there is provided an image processing device, comprising: an inputting means which inputs an image data obtained by imaging a subject for a predetermined period of time with a medical imaging apparatus and is arranged in time series; a calculating means which calculates the amount of change between the pixel value of each pixel in the image data at a first time in the predetermined period of time and the pixel value of each pixel in the image data at a second time in the predetermined period of time; a calculating means which calculates an average value of the pixel values from the first time to the second time for each pixel coordinate position, with respect to each pixel in the region where the amount of change is a predetermined value or less; and a producing means which produces a processed image in which the pixel value of each pixel in the region where the amount of change is the predetermined value or less has the average value and the pixel value of each pixel in the region where the amount of change is more than the predetermined value has the pixel value of the image data.

In another aspect of this disclosure, there is provided computer aided detection comprising a medical imaging apparatus which obtains an image data arranged in time series by imaging a subject for a predetermined period of time, an operation device which constructs a two-dimensional or three-dimensional image based on the image data, and a displaying device which displays an image produced by the operation device, wherein the operation device comprises: an inputting means which inputs the image data arranged in time series; an extracting along the time axis means which extracts, with respect to each pixel in the image data, pixels satisfying a predetermined condition from all the pixels arranged in time series for each pixel coordinate position along the time axis; and a constructing means which constructs a two-dimensional or three-dimensional image based on the pixels extracted along the time axis by the extracting along the time axis means, and wherein the displaying device displays a two-dimensional or three-dimensional image constructed by the constructing means.

In another aspect of this disclosure, there is provided computer aided detection comprising: a medical imaging apparatus which obtains an image data arranged in time series by imaging a subject for a predetermined period of time; an operation device which constructs a two-dimensional or three-dimensional image based on the image data; and a displaying device which displays an image produced by the operation device, wherein the operation device comprises: an inputting means which inputs the image data which is obtained by imaging a subject into which a contrast medium is injected for a predetermined period of time with a medical imaging apparatus and is arranged in time series; an image reconstructing means which reconstructs three-dimensional images arranged in time series based on the image data; an extracting along the time axis means which extracts, with respect to each pixel constituting the three-dimensional image arranged in time series, a maximum value pixel which has a clearest contrasted image by the contrast medium and a minimum value pixel which has little or no residual contrast medium therein from all the pixels arranged in time series for each pixel coordinate position along the time axis; a constructing means which constructs a two-dimensional or three-dimensional image which has a clearest contrasted image by the contrast medium based on the maximum value pixel and a two-dimensional or three-dimensional image which has little or no residual contrast medium therein based on the minimum value pixel; a difference operation means which performs a difference operation on the two-dimensional or three-dimensional image which has a clearest contrasted image by the contrast medium and the two-dimensional or three-dimensional image which has little or no residual contrast medium therein; and a difference image producing means which produces a difference image based on the result of the difference operation, and wherein the displaying device displays the difference image produced by the difference image producing means.

In another aspect of this disclosure, there is provided computer aided detection comprising: a medical imaging apparatus which obtains an image data arranged in time series by imaging a subject for a predetermined period of time; an operation device which constructs a two-dimensional or three-dimensional image based on the image data; and a displaying device which displays an image produced by the operation device, wherein the operation device comprises: an inputting means which inputs the image data arranged in time series; a filtering along the time axis means which performs, with respect to each pixel in the image data, a filtering process to all the pixels arranged in time series for each pixel coordinate position along the time axis and perform a predetermined weighting along the time axis along the time series; and a constructing means which constructs a two-dimensional or three-dimensional image based on the image data on which the filtering process along the time axis was performed by the filtering along the time axis means, and wherein the displaying device displays the two-dimensional or three-dimensional image constructed by the constructing means.

In another aspect of this disclosure, there is provided a method for filtering along the time axis, comprising: an inputting step of inputting an image data which is obtained by imaging :subject for a predetermined period of time with a medical imaging apparatus and is arranged in time series; and a filtering along the time axis step of performing, with respect to each pixel in the image data, a filtering process on all the pixels arranged in time series for each pixel coordinate position along the time axis and perform a predetermined weighting along the time axis along the time series.

In another aspect of this disclosure, there is provided a method for filtering along the time axis, comprising: an inputting step of inputting an image data which is obtained by imaging a subject for a predetermined period of time with a medical imaging apparatus and is arranged in time series; and a filtering along the time axis step of performing, with respect to each pixel in the image data, a filtering process to all the pixels arranged in time series for each pixel coordinate position along the time axis and obtain a pixel value which represents each pixel coordinate position.

Accordingly, a site where a contrast medium preferably exists can be extracted from the image data taken along the time series along the time axis so that the images of the sites are synthesized to create a wide and clear image of the path through which the contrast medium passed. Thus, the angiographic images can be improved to be clearer and wider while reducing the influence of a contrasting effect which changes with time transition in imaging and keeping the reduced amount of the contrast medium to use.

Further, in order to reduce a fluctuation in a pixel value along the time series, a change of a pixel value in a two-dimensional or three-dimensional image is processed along the time axis to obtain a filter function along the time axis. Application of the filter function along the time axis to the region of an image where the pixel value does not substantially change along the time series reduces the influence of noise without lowering concentration resolution and space resolution.

In addition, only a region where a contrast medium exists can be extracted by means of the difference between an image which is contrasted most by the contrast medium and an image where the contrast medium does not exist among the two-dimensional or three-dimensional images along the time series. Thus, when a certain organ surrounded by other organs should be extracted, a desired region can be accurately extracted in a short operating time by a simple process without any variations in extraction accuracy of a region caused by the differences in individual abilities among operators. A display of a contrasted image can be provided which does not have uneven results caused by an error in imaging timings or imaging locations or the concentration value of a contrast medium without changing the conventional amount of a contrast medium, and any increase of an amount of X-ray to which a subject is exposed by starting the imaging all over again and any increase of cost can be prevented.

Further, the filter function along the time axis makes it easier to know the state of a dynamic region by displaying an image of the dynamic region with colors while reducing the amount of noise. Thus, an image processing technique which makes the evaluation of function information underlying the dynamic region easier can be provided.

BRIEF DESCRIPTION OF THE DRAWINGS

FIG. 3 is a schematic diagram to show the way to produce a maximum value image from the fluctuations of pixel values time dependently in a blood vessel into which a contrast medium is injected;

FIG. 10 is a schematic diagram to show a state to perform a filtering process along the time axis on two-dimensional image data;

FIG. 12 is a flow chart to show a step to extract a contrasted blood vessel or an outer shell of contrasted blood flow in a contrasted organ according to the present invention;

DESCRIPTION OF SYMBOLS

Figure 1A:
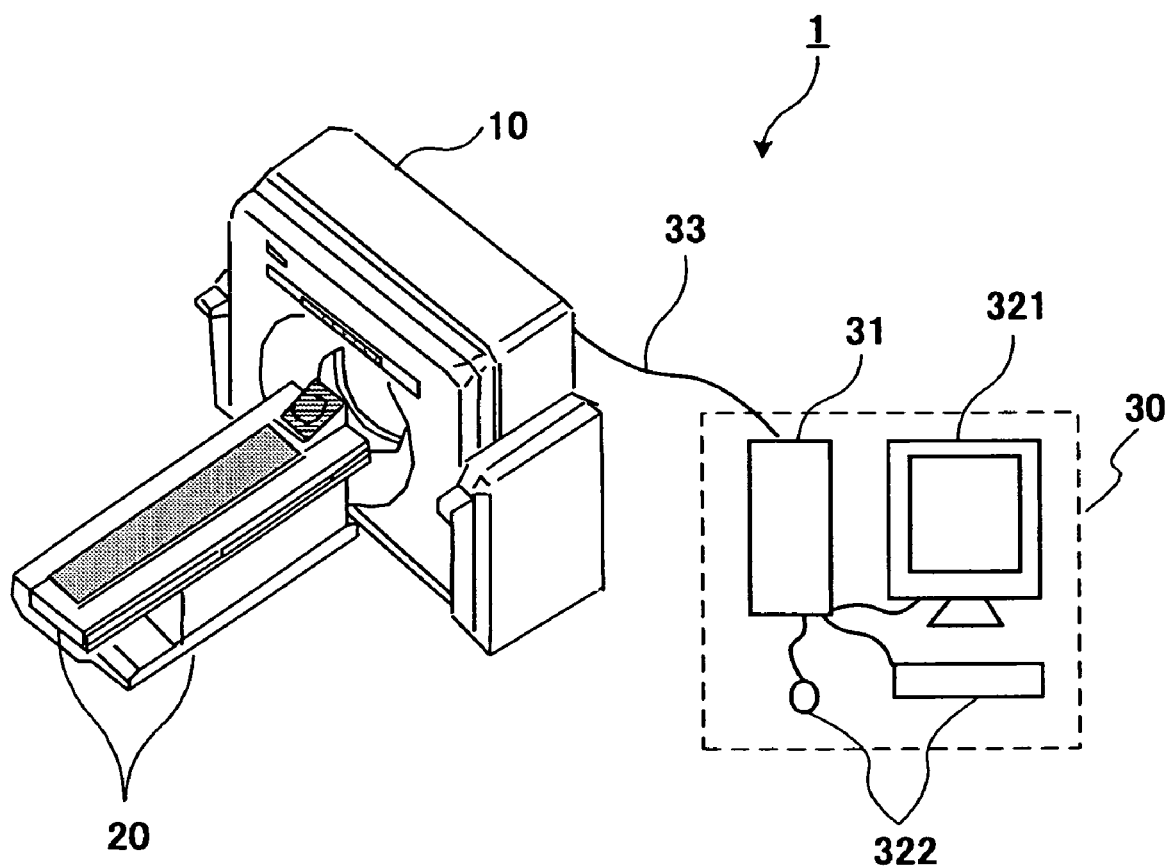
FIG. 1(a) is an entire structural diagram to show an X-ray CT apparatus of one embodiment according to the present invention.

1 X-ray CT apparatus
2 subject
3 medical imaging apparatus
4 MRI apparatus
5 network
6 image DB
10 scanner
51 contrasted blood vessel
52 contrast medium
53 maximum value image
54 minimum value image
61 three-dimensional image data at a time t1
62 three-dimensional image data at a time t2
63 three-dimensional image data at a time t3
64 three-dimensional image data at a time tn
65 three-dimensional image data into which maximum value pixels are collected from time t1 to time tn
71 two-dimensional image data at a time t1
72 two-dimensional image data at a time t2
73 two-dimensional image data at a time t3
74 two-dimensional image data at a time tn
75 two-dimensional image data into which maximum value pixels are collected from time t1 to time tn
81 three-dimensional image data
82 filtering process
83 image data after filtering process
91 three-dimensional image data at a time t1
92 three-dimensional image data at a time t2
93 three-dimensional image data at a time t3
94 three-dimensional image data at a time tn
95 three-dimensional image data after a process of weighting filter along the time axis
96 weighting filter along the time axis
101 two-dimensional image data at a time t1
102 two-dimensional image data at a time t2
103 two-dimensional image data at a time t3
104 two-dimensional image data at a time tn
105 two-dimensional image data after processing of weighting filter along the time axis
106 weighting filter along the time axis

BEST MODE FOR CARRYING OUT THE INVENTION

Now, embodiments of the present invention will be explained in detail with reference to the accompanying drawings.

Figure 1B:
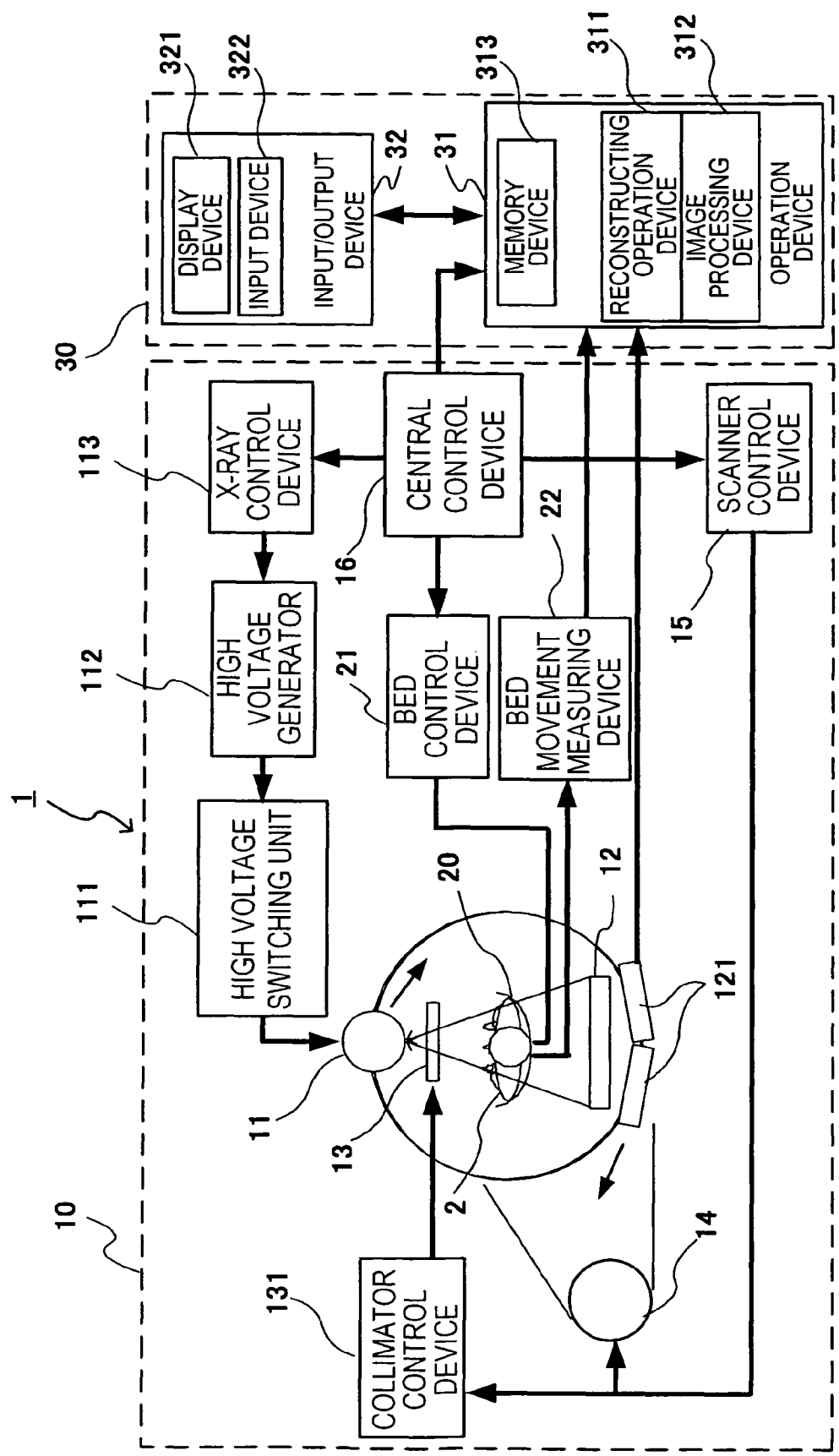
FIG. 1(b) is a block diagram to show the interior of the X-ray CT apparatus of one embodiment according to the present invention by separating in each function.

FIG. 1(a) is an entire structural diagram to show an X-ray CT apparatus of one embodiment according to the present invention, and FIG. 1(b) is a block diagram to show the interior of the X-ray CT apparatus of one embodiment according to the present invention by separating in each function.

The X-ray CT apparatus 1 in FIGS. 1(a) and 1(b) is mainly configured to include a scanner 10, an processing unit 30, and a power source/signal line 33 which connects between the scanner 10 and the processing unit 30.

The scanner 10 includes an X-ray source which contains an X-ray generator 11, a high voltage switching unit 111, a high voltage generator 112, and X-ray control device 113, a bed 20 on which a subject 2 is rested, an X-ray detector 12 which is placed across the subject 2 from the X-ray source, and a preamplifier 121 which converts and amplifies the X-ray detected by the X-ray detector 12 into an electric current to output it as a projected data signal into an operation device 31. The scanner 10 also includes a limiting means comprising of a collimator 13 and a collimator control device 131 which are placed between the X-ray source and a subject 2 to limit the X-ray.

The scanner 10 also includes a driving device 14 which circumferentially rotates the scanner 10 which is positioned around the subject 2, a scanner control device 15, and a central control device 16 which controls these elements.

When an operator inputs imaging conditions, for example, a velocity to move the bed, a tube current value, a tube voltage value, and a slice location, or reconstructing conditions (a reconstructing high quality mode, a reconstructing high-speed mode, a reconstructing interval, a reconstructing FOV, an image size, and the like) from an input unit 322 which includes a pointing device such as a mouse and a key board, based on the imaging conditions, the central control device 16 sends a control signal which is required for imaging to the X-ray control device 113, the bed control device 21 and the scanner control device 15. Upon receiving the signal to start an imaging, the X-ray CT apparatus 1 starts an imaging. As the imaging is started, the X-ray control device 113 sends a control signal to the high voltage generator 112 so that a high voltage is applied to the X-ray generator 11 via the high voltage switching unit 111. Then the X-ray generator 11 irradiates X-ray to the subject 2.

At the same time, the scanner control device 15 sends a control signal to the driving device 14. This causes the X-ray generator 11, the X-ray detector 12, and the preamplifier 121 to circumferentially rotate around the subject 2.

The bed control device 21 keeps the bed 20 with the subject 2 thereon fixed during a dynamic scan, and moves the bed parallel to the direction of a circumferential axis of the X-ray generator 11 during a helical scan. The moving velocity of the parallel movement of the bed 20 is measured by a bed movement measuring device 22 and is input to the operation device 31. For fluoroscopy (imaging of a flat perspective image of the subject 2), only the bed 20 is moved parallel to the direction along the circumferential axis while the X-ray generator 11, the X-ray detector 12 and the preamplifier 121 are kept fixed.

The X-ray from the X-ray generator 11 is irradiated to a region which is limited by the limiting means such as the collimator 13. The X-ray transmitted through the subject 2 is detected by the X-ray detector 12. The X-ray detected by the X-ray detector 12 is conversed into an electric current and is amplified by the preamplifier 121, and then is input to the operation device 31 as a projected data signal.

The processing unit 30 includes an operation device 31 to perform an image reconstructing process or the other image processes, and an input/output device 32 having an input device 322 of a pointing device such as a mouse and a keyboard and a displaying device 321 such as a CRT.

The operation device 31 includes an reconstructing operation device 311 to perform an image reconstructing process, an image processing device 322 to perform another image process, and a memory device 313 to store required data.

The reconstructing operation device 311 performs a reconstructing process based on the projected data signal input to the operation device 31 to generate a reconstructed image. The image processing device 312 performs an imaging process on the reconstructed image to store the reconstructed image after the image process into the memory device 313 and also display it on the displaying device 321 as a CT image.

Recent high performance X-ray CT apparatuses have been developed to enlarge a range for imaging at one time, improve a scan speed, improve a spatial resolution along body axis, and improve a time resolution in order to obtain an image with high time resolution and/or high space resolution in a short time. Such improved performance makes it possible to obtain a three-dimensional image data arranged in time series, that is, an image data expressed by a four coordinates of three-dimensional spatial coordinates and a time coordinate.

In addition, after a contrast medium such as iodine is injected into a subject 2, an imaging at the timing of the arrival of the contrast medium to an examination site makes it possible to obtain a highly contrasted image of the examination site.

Figure 2A:
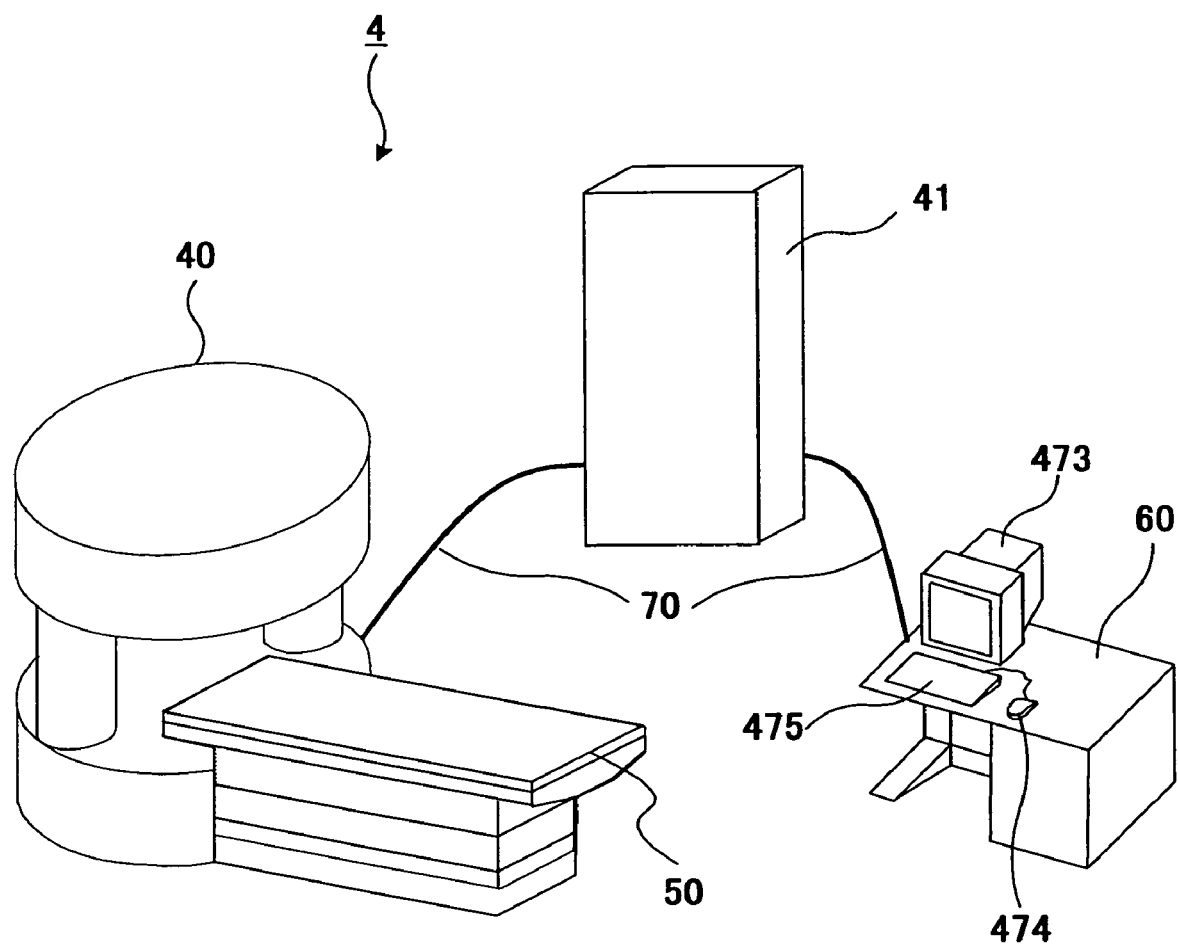
FIG. 2(a) is an entire structural diagram to show an MRI apparatus of one embodiment according to the present invention.
Figure 2B:
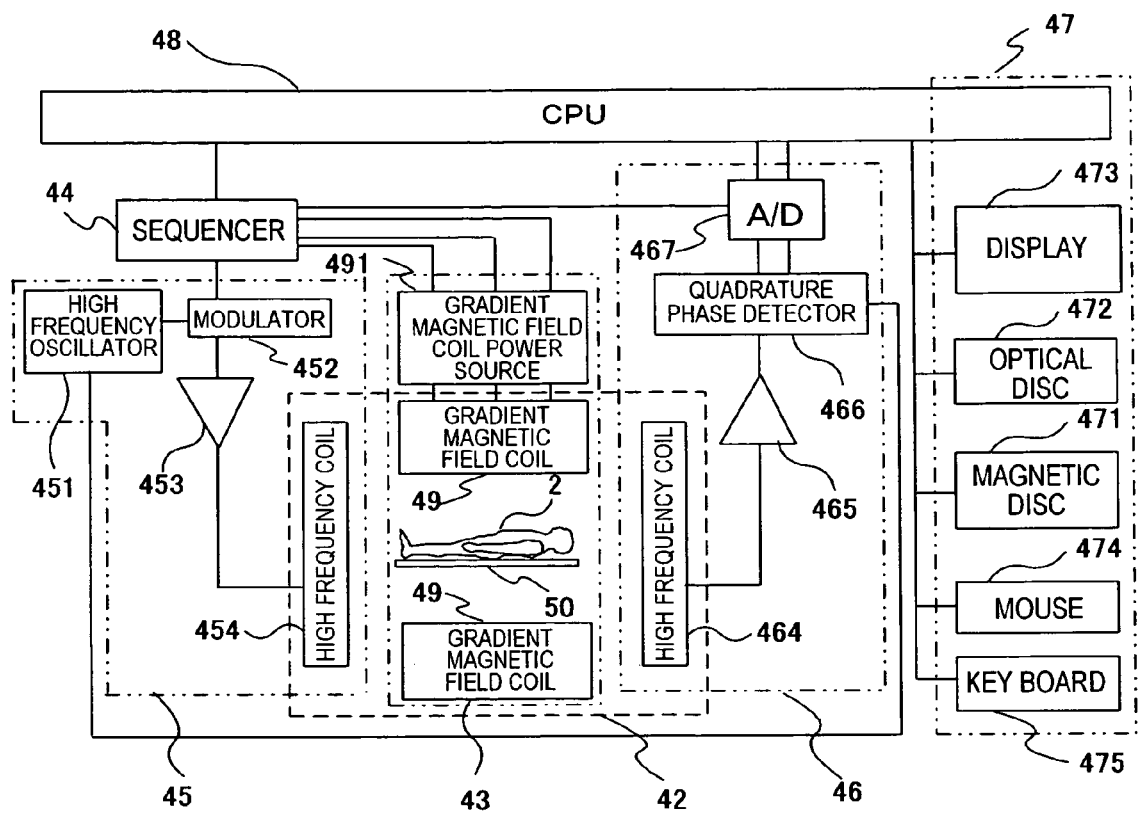
FIG. 2(b) is a block diagram to show the interior of the MRI apparatus of one embodiment according to the present invention by separating in each function.

Next, referring to FIGS. 2(*a*) and 2(*b*), an MRI apparatus of one embodiment according to the present invention will be explained. FIG. 2(*a*) is an entire structural diagram to show an MRI apparatus of one embodiment according to the present invention, and FIG. 2(*b*) is a block diagram to show the interior of the MRI apparatus of one embodiment according to the present invention by separating in each function.

The MRI apparatus 4 of FIG. 2 is of a perpendicular magnetic field type (open type), but may be of any other type such as a tunnel type.

In the MRI apparatus 4, a vibrating magnetic field (electromagnetic waves) is applied to a subject 2 arranged in static magnetic fields to induce nuclear magnetic resonance (NMR). A detecting coil (RF coil) detects resonance signals as electrical signals, thereby the signals are reconstructed as projected data to produce an image of the interior of the subject 2 noninvasively.

The MRI apparatus 4 comprises a gantry 40, a house 41 in which a power source to drive various devices in the gantry 40 and various control devices to control are stored, a bed 50 on which the above subject 2 is rested, and a processing unit 60 which processes the received NMR signals to reconstruct a tomogram image of the subject 2. The gantry 40 and the house 41 are connected by a power source/signal line 70. Similarly, the processing unit 60 and the house 41 are connected by a power source/signal line 70.

The gantry 40 and the bed 50 are placed in a shield room to shield high frequency electromagnetic waves and static magnetic fields (not shown). The house 41 and the processing unit 60 are placed outside of the shield room.

Next, referring to FIG. 2(*b*), the structure of the MRI apparatus 4 will be explained in more detail. The MRI apparatus 4 includes a static magnetic field generating system 42, a magnetic field gradient generating system 43, a sequencer 44, a transmitting system 45, a receiving system 46, a signal processing system 47 including an operating section, and a central processing unit (CPU) 48.

The static magnetic field generating system 42 generates a uniform static magnetic field around the subject 2 in a direction of the body axis of the subject 2 or in a direction orthogonal to the body axis of the subject 2. The static magnetic field generating system 42 comprises permanent magnet type, resistive type or superconductive type magnetic field generating means placed in the extended space around the subject 2.

The magnetic field gradient generating system 43 comprises two gradient magnetic field coils 49 which are wound in the three X, Y and Z axis directions, and a gradient magnetic field power source 491 to drive each gradient magnetic field coils 49. When the gradient magnetic field coil power source 491 for each gradient magnetic field coils 49 is driven by a commend from the sequencer 44 which will be explained below, gradient magnetic fields GX, GY, and GZ in the three X, Y and Z axis directions are applied to the subject 2. The way to apply the gradient magnetic fields sets a slice plane relative to the subject 2.

The sequencer 44 repeatedly applies high frequency magnetic field pulses which cause the atomic nucleus of an atom that produces a living tissue of the subject 2 to induce nuclear magnetic resonance, in a predetermined pulse sequence. The sequencer 44 is controlled to operate by the CPU 48, and sends various commands required to collect data of tomogram images of the subject 2 to the transmitting system 45, the magnetic field gradient generating system 43, and a receiving system 46.

The transmitting system 45 irradiates a high frequency magnetic field which causes the atomic nucleus of an atom that produces a living tissue of the subject 2 to induce nuclear magnetic resonance with a high frequency pulses emitted from the sequencer 44. The transmitting system 45 includes a high frequency oscillator 451, a modulator 452, a high frequency amplifier 453, and a high frequency coil 454 for transmitting. The high frequency pulses emitted from the high frequency oscillator 451 are amplitude modulated by the modulator 452 according to the command from the sequencer 44. After the amplitude modulated high frequency pulses are amplified by the high frequency amplifier 453, the pulses are supplied to the high frequency coil 454 positioned close to the subject 2. In this way, an electromagnetic wave is irradiated to the subject 2.

The receiving system 46 detects an echo signal (NMR signal) emitted by the nuclear magnetic resonance in atomic nucleus of the living tissue of the subject 2. The receiving system 46 comprises a high frequency coil 464 for receiving, an amplifier 465, a quadrature phase detector 466, and an A/D converter 467. The electromagnetic wave (NMR signal) from the subject 2 in response to the electromagnetic waves emitted from the high frequency coil 454 for transmitting is detected by the high frequency coil 464 positioned close to the subject 2. The detected NMR signal is input into the A/D converter 467 via the amplifier 465 and the quadrature phase detector 466 to be converted into a digital signal. The quadrature phase detector 466 converts the detected NMR signal into biserial data collected by sampling at timings specified by the command from the sequencer 44. The collected data is transmitted to the signal processing system 47.

The signal processing system 47 includes a CPU 48, a recording device such as a magnetic disc 471 and an optical disc 472, a display 473 such as a CRT, a pointing device and its controller such as a mouse 474, and an input unit such as a key board 475. The CPU 48 performs a Fourier transform operation and an operation of correction coefficient calculation for image reconstruction, and performs appropriate operations based on a signal strength distribution or a plurality of signals of any section to obtain a distribution to create an image, thereby generates a tomogram. The display 473 displays the tomogram.

Such a MRI apparatus 4 with the recent increased performance produces a high magnetic field (e.g. 1.5 T (tesla)) apparatus, which allows four dimensional image data to be obtained with noise of a practical level and high time resolution.

The MRI apparatus 4 with the use of a contrast medium provides an image with a high contrast at an examination site.

EXAMPLE 1

Figure 4:
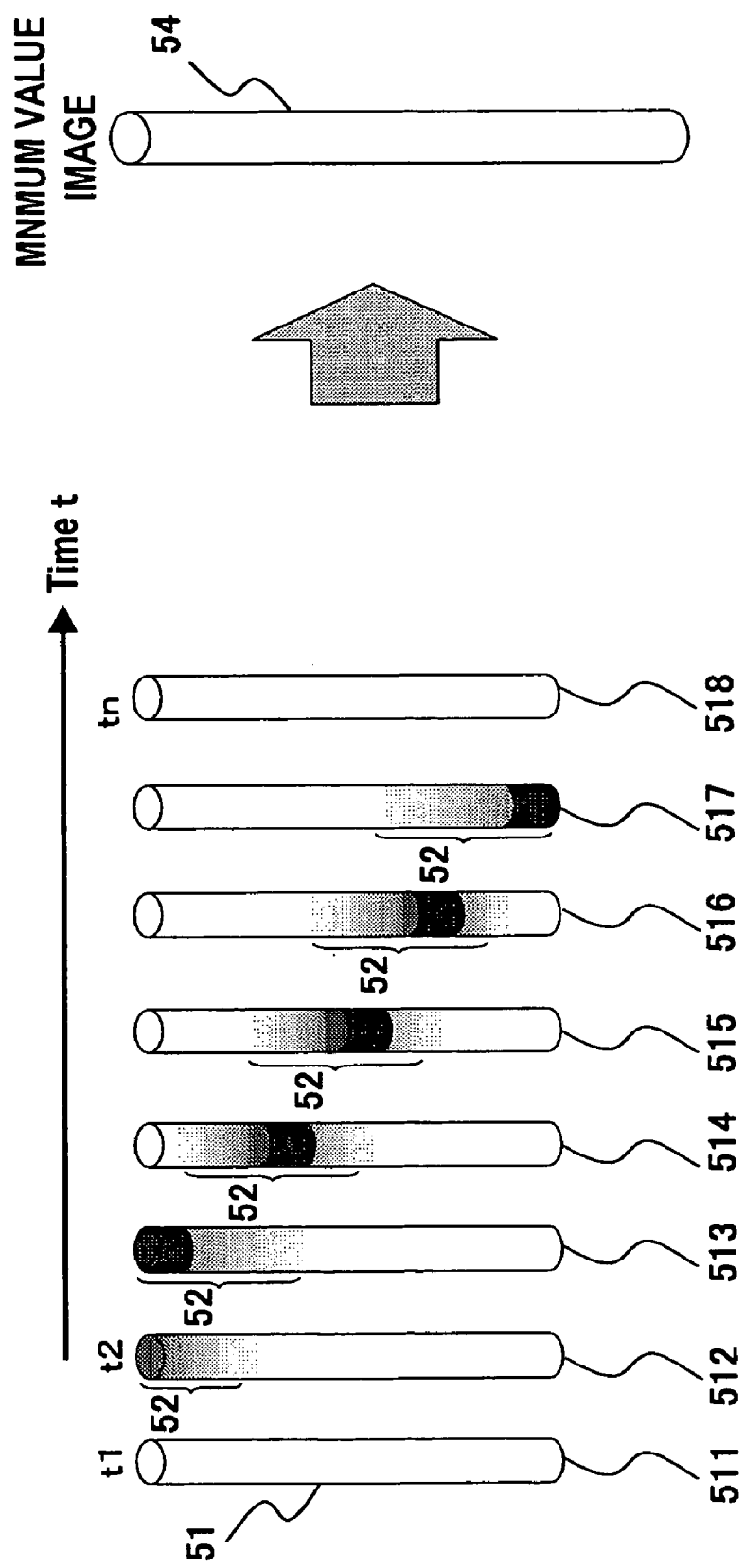
FIG. 4 is a schematic diagram to show the way to produce a minimum value image from the fluctuations of pixel values time dependently in a blood vessel into which a contrast medium is injected.
Figure 5:
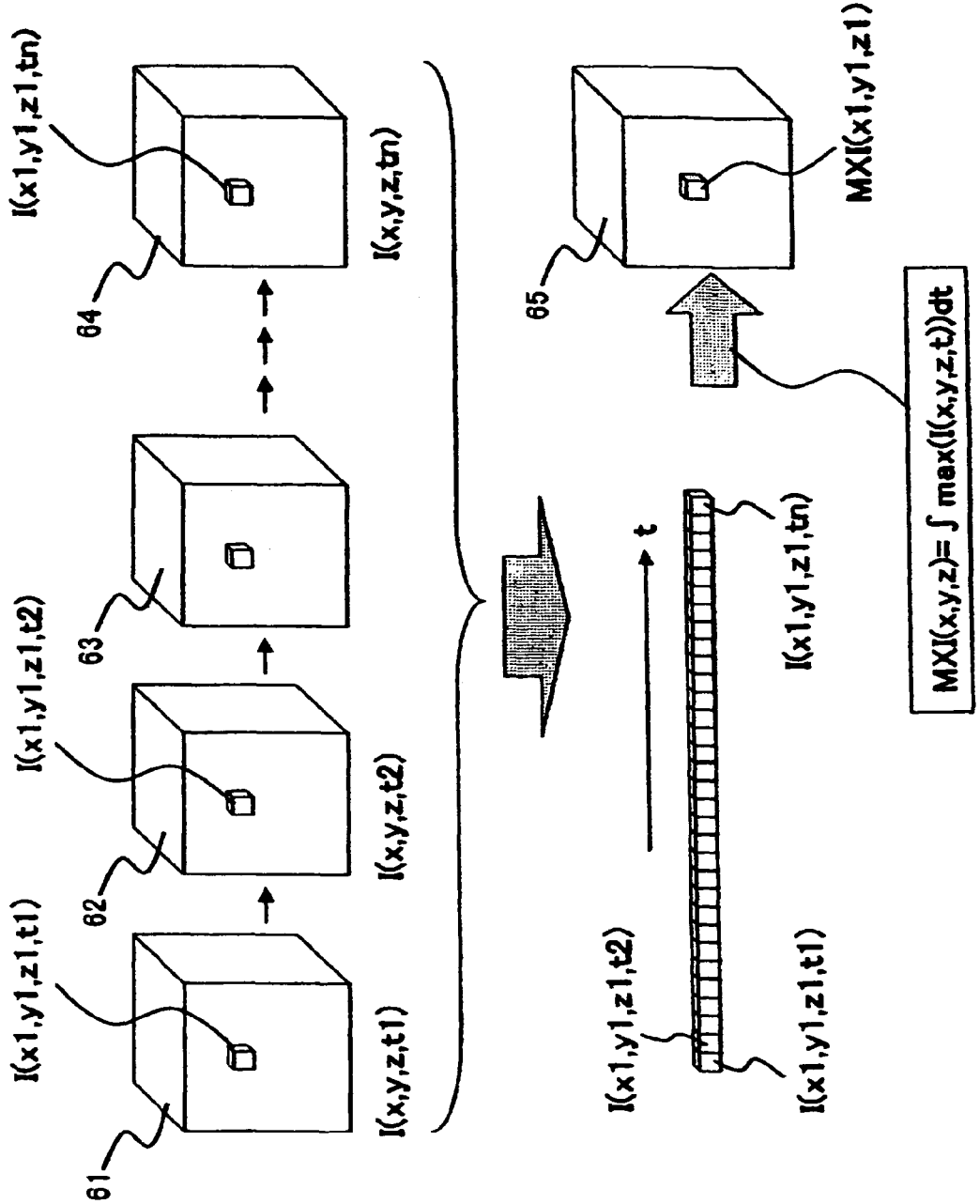
FIG. 5 is a schematic diagram to show a method to obtain an image the pixel value of which has the maximum value time dependently in three-dimensional image data.

Next, referring to FIG. 3 to FIG. 5, a first embodiment of the present invention will be explained. FIG. 3 is a schematic diagram to show the way to produce a maximum value image from the fluctuations of pixel values time dependently in a blood vessel into which a contrast medium is injected. FIG. 4 is a schematic diagram to show the way to produce a minimum value image from the fluctuations of pixel values time dependently in a blood vessel into which a contrast medium is injected. FIG. 5 is a schematic diagram to show a method to obtain an image the pixel value of which has the maximum value MXI time dependently.

FIG. 3 to FIG. 5 show the first embodiment of the present invention, and a step to produce a maximum value image 53 and a minimum value image 54 in the three-dimensional image data arranged in time series.

A predetermined range is set as a region of interest in the image data obtained by the X-ray CT apparatus 1 of FIG. 1 or the two-dimensional image (cross-section image) data or three-dimensional image data of a predetermined range of a subject 2 which are reconstructed based on an image data which are taken in time series by the MRI apparatus 4 of FIG. 2. The region of interest is set by specifying a range in the reconstructed image displayed on the displaying device 321 or 473 by dragging a predetermined region with the mouse 322 or 474.

In Example 1, an image processing is performed based on the pixels constituting a region of interest in a reconstructed image, but the image processing may be performed based on the pixels constituting the entire reconstructed image. Alternatively, instead of a reconstructed image, a projected image by a X-ray equipment may be used.

FIG. 3 to FIG. 4 show a blood vessel in the region which is set as a region of interest. FIG. 5 is the image data constituting the above region of interest, and the pixel I (X,Y,Z) shows the coordinate of a pixel in the region of interest. In FIG. 3 to FIG. 4, reference numeral 51 denotes a contrasted blood vessel, and reference numeral 52 denotes a contrast medium. The contrasted blood vessel 51 is a three-dimensional image reconstructed based on an image data obtained by the X-ray CT apparatus 1 or the MRI apparatus 4.

In FIG. 3 to FIG. 4, reference numerals 511 to 518 show a contrasted blood vessel after a predetermined period of time sequentially passes after a contrast medium was injected. In FIG. 3 to FIG. 4, reference numerals 511 shows the contrasted blood vessel 51 at a time t1, and reference numerals 512 shows the contrasted blood vessel 51 at a time t2, and so on with the contrasted blood vessel 513 to 518, and reference numerals 518 shows the contrasted blood vessel 51 at a time tn. In FIG. 3 and FIG. 4, the states of fluctuation of the pixel value in the contrasted blood vessel 51 after the contrast medium 52 was injected are shown by shading. The maximum value image 53 is the resulting image by applying the present invention, and is the contrasted blood vessel fulfilled with the contrast medium, that is, a three-dimensional image with the most clear tomogram. The minimum value image 54 in FIG. 4 is the resulting image by applying the present invention, and is the contrasted blood vessel without the contrast medium therein, that is, a three-dimensional image without a contrasted image by the effect of the contrast medium.

Herein, the length of time that elapses after the injection of the contrast medium 52 is in the relation of t1<t2< . . . <tn.

As the time elapses from time t1 to time tn, since the contrast medium 52 moves in the blood vessel from the upper to the lower in FIG. 3 and FIG. 4, the location with the maximum pixel value in the contrasted blood vessel 51 also moves accordingly. Thus, the image of the contrasted blood vessel 51 at a certain time is shown with a different shading of the contrasted unevenness like the one of those 512 to 517.

In FIG. 3, the pixel having the maximum value is extracted along the time axis between time t1 and time tn for each pixel coordinate position with respect to all the pixels constituting the contrasted blood vessel 51. Then the pixels extracted along the time axis are collected to obtain the maximum value image 53.

Referring to FIG. 5, the way to obtain a maximum value image will be explained.

Reference numerals 61 to 64 in FIG. 5 denote three-dimensional image data arranged in time series. Each of the three-dimensional image data contains a pixel I (X,Y,Z) which corresponds to the same pixel coordinate position at a certain time. In other words, a set of the pixels I (X,Y,Z) is the three-dimensional image data 61 to 64.

Each pixel is expressed by a four dimensional coordinates of three-dimensional spatial coordinates and a time coordinate.

For example, in an I (X,Y,Z,tn) in the image data 64, the X, Y, and Z represent coordinates of a three-dimensional position, and the tn represents an elapsed time after the injection of a contrast medium.

The medical imaging apparatus shown in FIG. 1 and FIG. 2 is driven to start imaging of the subject 2. Once the imgaing is started, the contrast medium 52 is injected in a blood vessel of the subject 2.

Herein, the MXI (X1,Y1,Z1) in the three-dimensional image data 65 is the maximum value pixel to be obtained.

Formula 1 is a function along the time axis to extract a pixel along the time axis which corresponds to the maximum value in the pixel values for a predetermined period of time, that is from time t1 to time tn, for each pixel coordinate position with respect each pixel in the three-dimensional image data arranged in time series.

$$MXI(X,Y,Z) = \int max(I(X,Y,Z,t))dt \quad \text{[Formula 1]}$$

As shown in FIG. 5, the initial maximum value pixel at a spatial coordinate (X,Y,Z) is set to be the pixel value at a time t1, MXI (X,Y,Z)=I (X,Y,Z,t1). At this point of time, the contrast medium 52 has not reached the range to be taken.

Gradually, the contrast medium 52 flows into the range to be taken. For example, as time elapses, when the pixel value of the three-dimensional image data MXI (X,Y,Z) is smaller than I (X,Y,Z,t1), the maximum value pixel is replaced to satisfy MXI (X,Y,Z)=I (X,Y,Z,t).

By comparing the data with the maximum value pixel from beginning time t1 to last time tn for each pixel coordinate position defined by the coordinate of X,Y, and Z, an image MXI (X,Y,Z) is obtained where the pixel value is the maximum value time dependently.

In this way, the maximum values along the time axis for each pixel coordinate position are obtained, and when the maximum values are arranged in each three-dimensional pixel coordinate position, a maximum value image 53 is completed.

Application of this method to the contrasted blood vessel 51 provides an entire image of the contrasted blood vessel 51 which is clear without unevenness due to emptiness of contrast medium 52.

Next, the method to produce a minimum value image 54 where the pixel value is the minimum value along the time axis for each pixel will be explained.

Similar to the operation shown in FIG. 3 and FIG. 5, the initial minimum value pixel at a spatial coordinate (X,Y,Z) is set to be the pixel value at a time t1, MNI (X,Y,Z)=I (X,Y,Z, t1). Then, the initial minimum value pixel is compared with the pixel values at a time t2, . . . and tn sequentially, and when MNI (X,Y,Z) is smaller than I (X,Y,Z,t), the minimum value pixel is replaced to satisfy MNI (X,Y,Z)=I (X,Y,Z,t). This operation is repeated for each pixel until the three-dimensional image data at the last time tn to collect the minimum value pixels.

When the minimum value pixels are arranged in each three-dimensional pixel coordinate position, a minimum value image 54 is completed.

Application of this method to the contrasted blood vessel provides an entire image of the non-contrasted blood vessel which is clear without unevenness.

A pixel in a time zone can be clipped by applying a window function along the time axis to weight along the time axis. Since the contrast medium 52 flows in artery and in vein at different times, only the artery can be extracted by excluding the vein by clipping the pixels in a certain time zone. That is, the site to be extracted can be limited by utilizing a time difference such as that in the entrance of the contrast medium.

Next, the way to obtain a difference between the maximum value image 53 and the minimum value image 54 will be explained. The difference is not necessarily have to be obtained, and the above maximum value image 53 and the minimum value image 54 can be used as they are. For simplicity, in this embodiment, the explanation below will be made as the object being immovable.

The contrast medium 52 in a range to be taken is imaged without a change in shading, by a subtraction between the corresponding pixels of the above maximum value image 53 and the minimum value image 54 for each pixel coordinate position defined by a three-dimensional coordinate (X,Y,Z).

Since the blood flow distribution amount in the imaged contrast medium 52 shows the blood flow path of the same shape, the blood flow path (lumen of blood vessel) can be accurately evaluated.

As described above, in the prior art, it was difficult to obtain an accurate image due to a different result depending on setting of a threshold value, for the image is displayed by excluding the parts other than of blood flow by the threshold value or a region growing technique. To the contrary, according to the present invention, without a setting of a threshold value or a complicated calculation such as a region growing technique, a simple subtraction allows a path of the contrast medium 52, that is the shape of a blood flow path (lumen of blood vessel) to be accurately imaged.

If the object to be taken is moving, positions of the object are associated each other at each time so that operations are performed between the associated pixels. The methods to associate positions of a moving object include, for example, a method to extract a characteristic amount such as a pixel value, center of gravity, a difference in space frequencies, or a differential value, and perform an affine transform operation such as a rotation, deformation or moving of an image based on the characteristic amount, so that image positions can be associated each other at a position in the same image matrix. This makes it possible to obtain an accurate path and shape of the contrast medium 52 even if the object is moving, and for example, the blood flow through coronary artery can be evaluated.

EXAMPLE 2

In the above Example 1, a contrasted image of a blood vessel is produced with an image data I (X,Y,Z,tn) consisting of four dimensional coordinates of a three-dimensional pixel coordinate position I (X,Y,Z) and time data, but a contrasted image of a blood vessel may be produced with image data I (X,Y,tn) consisting of three-dimensional coordinates of a two-dimensional pixel coordinate position I (X,Y) and time data.

Figure 6:
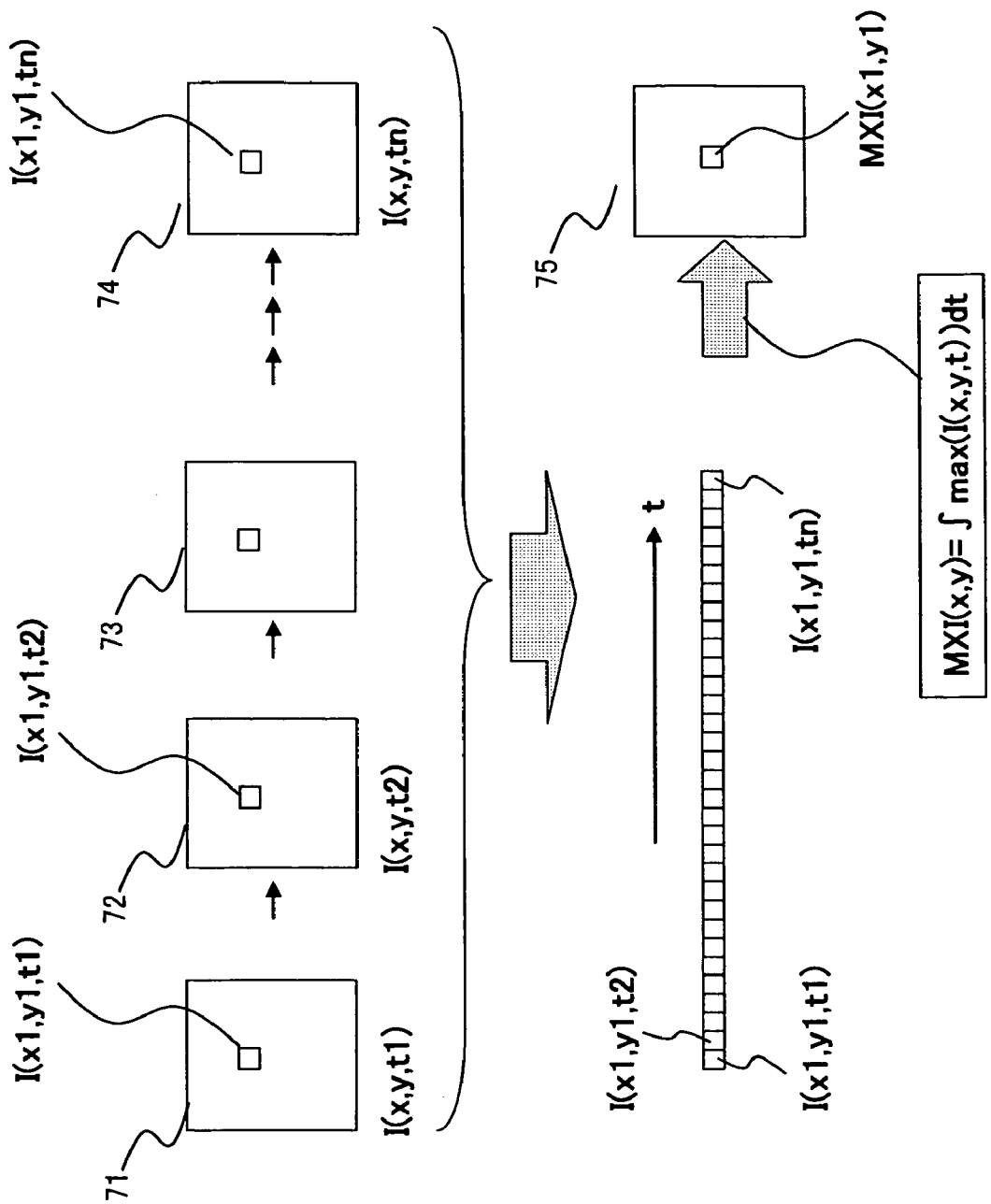
FIG. 6 is a schematic diagram to show a method to obtain an image the pixel value of which has the maximum value time dependently in two-dimensional image data.

Reference numerals 71 to 74 of FIG. 6 denote two-dimensional image data arranged in time series. Reference numeral 71 denotes two-dimensional image data at a time t1, reference numeral 72 denotes two-dimensional image data at a time t1, and reference numeral 74 denotes two-dimensional image data at a time tn.

The two-dimensional image data 75 is the maximum value pixel to be obtained.

Formula 2 is a function along the time axis to extract a pixel along the time axis which corresponds to the maximum value in the pixel values for a predetermined period of time, that is from time t1 to time tn, for each pixel coordinate position with respect each pixel in the two-dimensional image data arranged in time series.

$$MXI(X,Y) = \int max(I(X,Y,t))dt \quad \text{[Formula 2]}$$

As shown in FIG. 6, the initial maximum value pixel at a plane coordinate (X, Y) is set to be the pixel at a time t1, MXI (X,Y)=I (X,Y,t1). As time elapses, when the pixel value of the two-dimensional image data MXI (X,Y) is smaller than I (X,Y,t), the maximum value pixel is replaced to satisfy MXI (X,Y)=I (X,Y,t). The maximum value pixel is extracted along the time axis from the pixels between time t1 and time tn with respect to each pixel, and when the maximum value pixels are arranged in each two-dimensional pixel coordinate position, a maximum value image is completed.

Similarly, the initial minimum value pixel at a plane coordinate (X,Y) is set to be the pixel at a time t1, MNI (X,Y)=I (X,Y,t1). Then, as time elapses, when the pixel value of the two-dimensional image MNI (X,Y) is bigger than I (X,Y,t), the minimum value pixel is replaced to satisfy MNI (X,Y)=I (X,Y,t). The minimum value pixel is extracted along the time axis from the pixels between time t1 and time tn with respect to each pixel, and when the minimum value pixels are arranged in each two-dimensional coordinate, a minimum value image is completed.

EXAMPLE 3

In Example 3, a filtering process along the time axis is performed to three-dimensional image data arranged in time series.

A filtering along the time axis provides an image in which a space resolution and a time resolution are arbitrarily adjusted relative to a noise amount. The filtering also can visualize the amount of change in a concentration value along the time axis.

Figure 7:
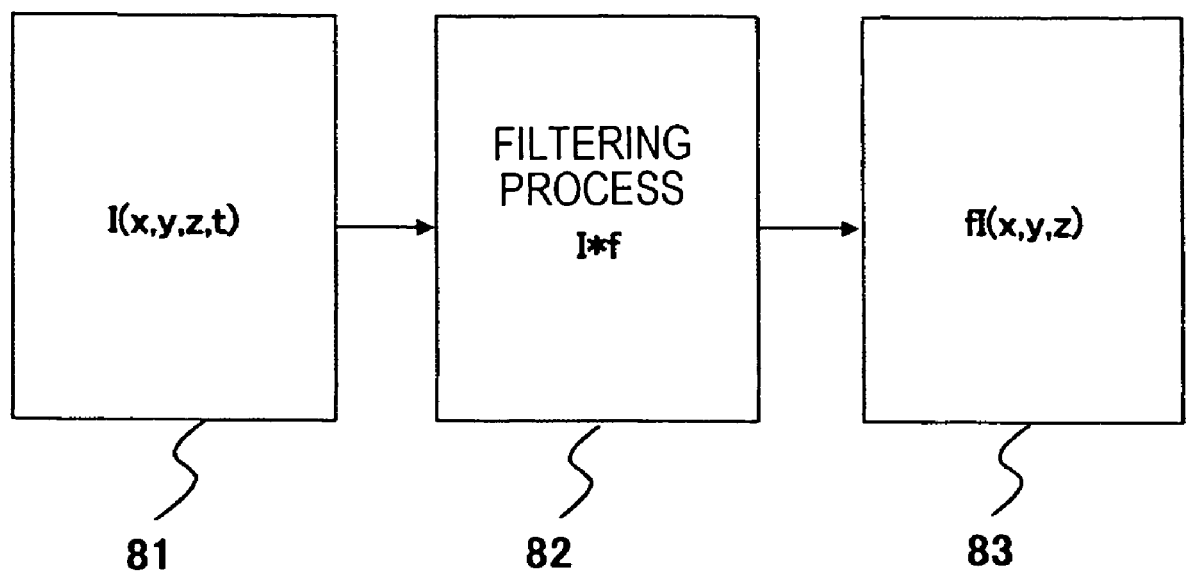
FIG. 7 is a schematic diagram to show a step to perform a filtering process along the time axis on three-dimensional image data.
Figure 8:
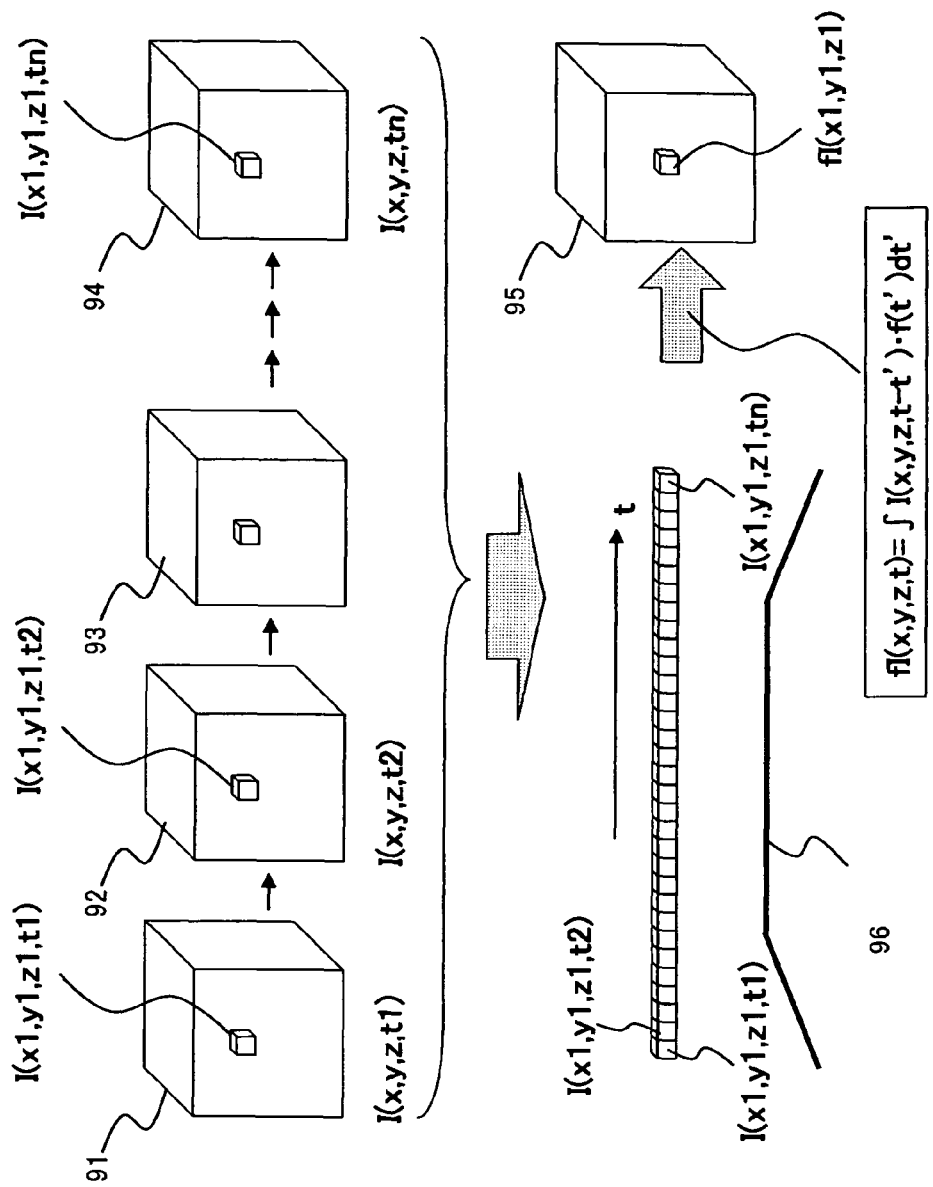
FIG. 8 is a schematic diagram to show a state to perform a filtering process along the time axis on three-dimensional image data.

Referring to FIG. 7 to FIG. 9, this embodiment will be explained. FIG. 7 is a schematic diagram to show a step to perform a filtering process along the time axis (along the time axis filter kernel) on three-dimensional image data arranged in time series.

Reference numeral 81 in FIG. 7 denotes a pixel I (X,Y,Z,t) which can be specified by a time coordinate and a spatial coordinate. Reference numeral 82 denotes a filtering process along the time axis. Reference numeral 83 denotes a filtering function along the time axis obtained by a filtering process on the pixel 81 along the time axis. Information along the time axis is used and integrated into fI (X,Y,Z) spatial coordinates.

Also in FIG. 8, a filtering process along the time axis is performed on the corresponding pixels in three-dimensional image data in different time phases. The results of the filtering process along the time axis are aggregated (added, in this case) to obtain a fI (X,Y,Z). Reference numerals 91 to 94 in FIG. 8 denote three-dimensional image data arranged in time series. Each of the three-dimensional image data contains a pixel I (X,Y,Z) which corresponds to the same pixel coordinate position. In other words, a set of the pixels I (X,Y,Z) is the three-dimensional image data 91 to 94.

This pixel is expressed by a four dimensional coordinates of three-dimensional spatial coordinates and a time coordinate.

For example, in an I (X,Y,Z,tn) in the image data 94, the X, Y, and Z represent coordinates of a three-dimensional position, and the tn represents an elapsed time after the injection of a contrast medium. Formula 3 is a function to perform a filtering process along the time axis (along the time axis filter kernel) along the time axis in the pixel values for a predetermined period of time, that is from time t1 to time tn, for each pixel coordinate position with respect each pixel in the three-dimensional image data arranged in time series, where f(t) is the filtering along the time axis (along the time axis filter kernel).

$$fI(X,Y,Z,t)=\int_{\infty}^{\infty}I(X,Y,Z,t-t')\bullet f(t')dt'$$ [Formula 3]

The medical imaging apparatus shown in FIG. 1 and FIG. 2 is driven to start imaging of the subject 2. Once the imaging is started, the contrast medium 52 is injected in the subject 2.

The fI (X1,Y1,Z1) in the three-dimensional image data 95 is the pixel into which the results of the filtering process along the time axis on the pixel coordinate position I (X1,Y1,Z1) are aggregated.

Now assume that the interested pixels are from I (X1,Y1,Z1,t1) to I (X1,Y1,Z1,tn). These pixels are the interested pixels I (X1,Y1,Z1) which are arranged time dependently from t1 to tn. Application of for example a trapezoidal shaped filter 96 along the time axis to the arrangement for adding provides the results fI of the filtering process along the time axis, and the results are collected to display an image.

In this Example, the method to perform a filtering process along the time axis by convolution in real space is used, but other methods which are mathematically equal to this such as a method to perform a filtering process along the time axis by Fourier transform in a frequency space may be used.

Next, referring to FIG. 9, the types of a filtering along the time axis, the way to create them in the present invention, and their effects will be explained. Reference N in FIG. 9 denotes a time of interest. The time of interest means a time phase to be imaged eventually.

(1) Sum Average Filter along the Time Axis

Figure 9A:
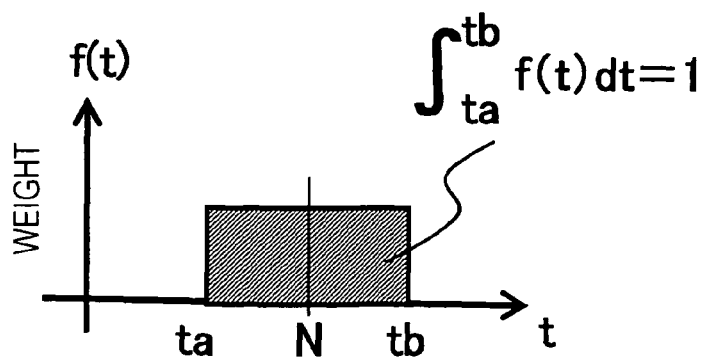
FIG. 9(a) is a schematic diagram to show an example of a sum average filter along the time axis.

Application of a sum average filter along the time axis as a the filter function along the time axis allows an image with reduced fluctuation of a pixel value along the time series to be acquired without lowering a space resolution, that is, allows an image with reduced noise to be acquired. In this case, a filter along the time axis such as that shown in FIG. 9(a) is superposed by putting an interested pixel at a time of interest N at the center. In other words, the result of the filtering process along the time axis by taking a sum average of the data around the time of interest is obtained as a display pixel for imaging. Such an image acquired in this way has less fluctuation.

(2) Weighted Sum Filter along the Time Axis

Figure 9B:
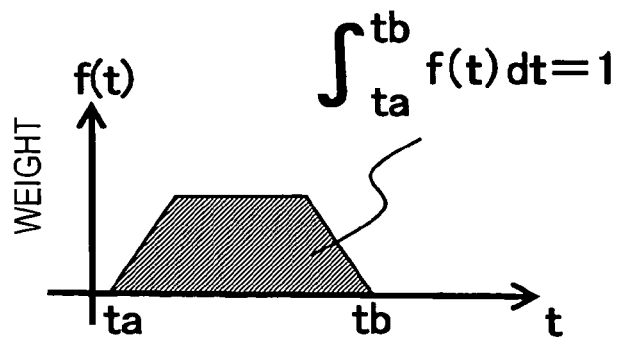
FIG. 9(b) is a schematic diagram to show an example of a sum average filter along the time axis.

Application of a weighted sum filter along the time axis as a filter function along the time axis allows, similar to the sum average filter along the time axis, an image with reduced fluctuation of a pixel value along the time series to be acquired without lowering a space resolution, that is, allows an image with reduced noise to be acquired. In this case, as shown in FIG. 9(b), the results of the filtering process along the time axis by multiplying the different time data at a same position by a trapezoid shaped weight which makes it possible to obtain more contribution at an interested position at a time of interest are added and collected for imaging. Such an image acquired in this way has less fluctuation.

(3) Median Filter along the Time Axis

Figure 9C:
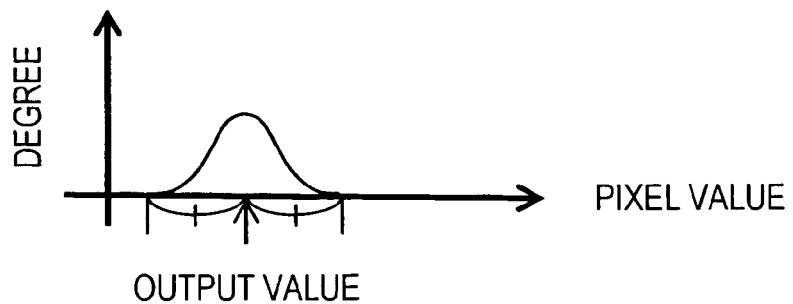
FIG. 9(c) is a schematic diagram to show an example of a median filter along the time axis.

This median filter along the time axis is a filter along the time axis to obtain the pixel value which comes to the center when the pixel values in a certain time range from ta to tb are arranged sequentially from the smallest to the largest as shown in FIG. 9(c) as a pixel value which represents each pixel coordinate position.

Application of the median filter along the time axis as a the filter function along the time axis allows, similar to the sum average filter along the time axis and the weighted sum filter along the time axis, an image with reduced fluctuation of a pixel value along the time series to be acquired without lowering a space resolution, that is, allows an image with reduced noise to be acquired. The median filter along the time axis can reduce spike-like (higher graininess) noises more effectively compared to the sum average filter along the time axis and the weighted sum filter along the time axis. Such an image acquired in this way has less spike-like fluctuation noises.

In the case of the median filter along the time axis, the pixel value which comes to the center when the pixel values in a certain time range from ta to tb are arranged sequentially from the smallest to the largest is output, but any pixel value can be output from the pixel values for each pixel arranged in time series for example by specifying the second largest pixel value to be output.

(4) Differential Filter along the Time Axis

Figure 9D:
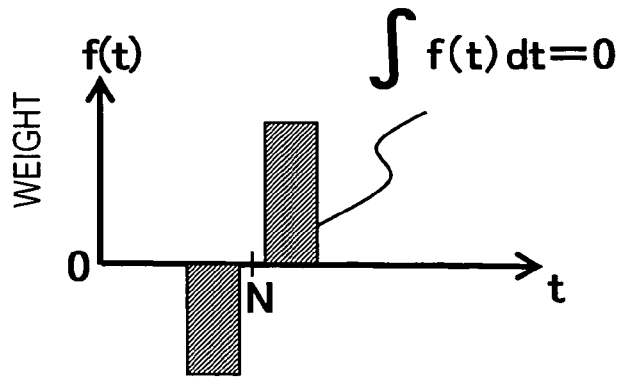
FIG. 9(d) is a schematic diagram to show an example of a differential filter along the time axis.

Application of the differential filter along the time axis as a filter function along the time axis allows a fluctuation amount between the target objects to be imaged (visualized) in different time phases. In this case, as shown in FIG. 9(d), the difference value between data at close times across a time of interest N is imaged as a result of the filter along the time axis.

(5) Preemphasis Filter along the Time Axis

Application of the preemphasis filter along the time axis as a filter function along the time axis allows an image with improved effective time resolution to be acquired.

Figure 9E:
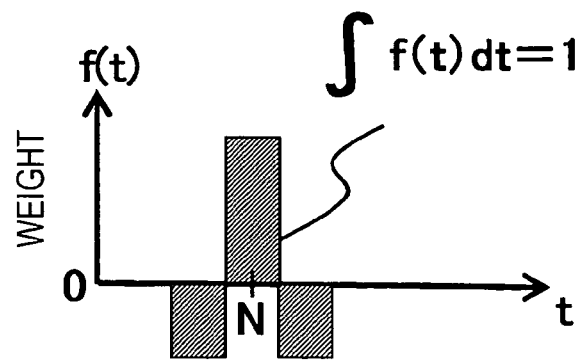
FIG. 9(e) is a schematic diagram to show an example of a preemphasis filter along the time axis.

In this case, as shown in FIG. 9(e), the product by multiplying a time of interest N by a high weight (positive weight) and the product by multiplying close data by a negative weight are added, so that the sum is imaged as a result of the filtering process along the time axis.

(6) High Order along the Time Axis Filter

The filter along the time axis may be a high order along the time axis filter which is a combination of a plurality of filters along the time axis. Alternatively, a window function may be used with a known filtering process to obtain a result at any time zone. For example, a combination of a similarity filter along the time axis and a median filter along the time axis can achieve a high degree of reduction of noise. Data at plurality of points which have pixel values close to the one at an time of interest are extracted along the time axis in a certain time range across the time of interest N, and the middle value of these is imaged as a result of the filtering process along the time axis.

(7) Similarity Filter along the Time Axis

A value obtained by sum averaging the data at plurality of points which have pixel values closer to the one at an time of interest position in a certain time range from ta to tb across the time of interest N is imaged as result of the filtering process along the time axis. In this case, the number of data to be sum-averaged may be any depending on the size of a filter along the time axis As described above, application of a filter along the time axis makes it possible to reduce noise. A filter along the time axis may be applied for each region of interest of an image or for the entire image.

EXAMPLE 4

In above Example 3, a filtering process along the time axis is performed based on an image data with four dimensional coordinates of three-dimensional spatial coordinates and a time coordinate. However, a filtering process along the time axis may be performed based on an image data with three-dimensional coordinates of two-dimensional spatial coordinates and a time coordinate.

In FIG. 10, an image 105 is acquired after filtering process along the time axis, for example by applying a trapezoidal filter along the time axis 106 to each pixel of two-dimensional image data 101, 102, 103, and 104 arranged in time series. The two-dimensional images 101, 102, 103, and 104 in FIG. 10 are expressed by three-dimensional coordinates I (X,Y,t) consisting of two-dimensional spatial coordinates (X,Y) and a time coordinate t. Similar to the above embodiment, a filtering process is performed along the time axis to obtain an image data 105 expressed by a three-dimensional coordinates which includes a time data as a result fI of the filter along the time axis.

Formula 4 is a function to perform a filtering process along the time axis (along the time axis filter kernel) along the time axis, for example by applying the above trapezoidal filter along the time axis 106 to pixel values from time t1 to time tn, where f(t) is the filter along the time axis (along the time axis filter kernel).

$$fI(X,Y,t) = \int_{-\infty}^{\infty} I(X,Y,t-t') \bullet f(t') dt' \qquad \text{[Formula 4]}$$

EXAMPLE 5

Referring to FIG. 11, Example 5 will be explained.

In Example 5, a clear image is provided by excluding noise which is generated when a two-dimensional image with a movable object is displayed time dependently.

Figure 11A:
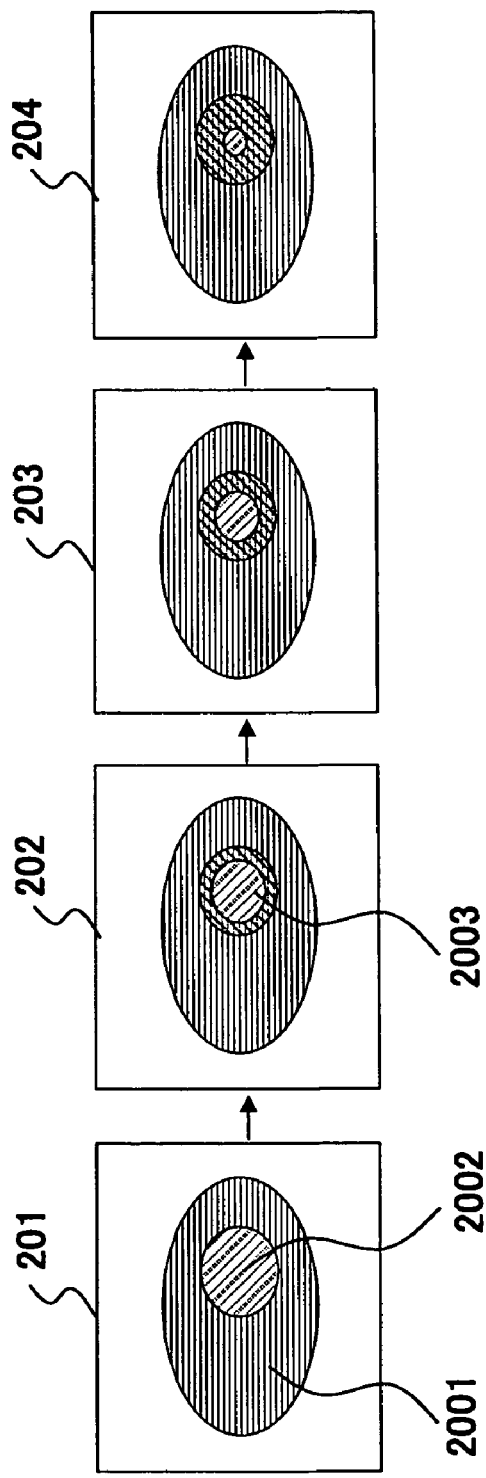
FIG. 11(a) is a schematic diagram to show an example of a cineangiogram the pixel value of which changes time dependently as the object moves.
Figure 11B:
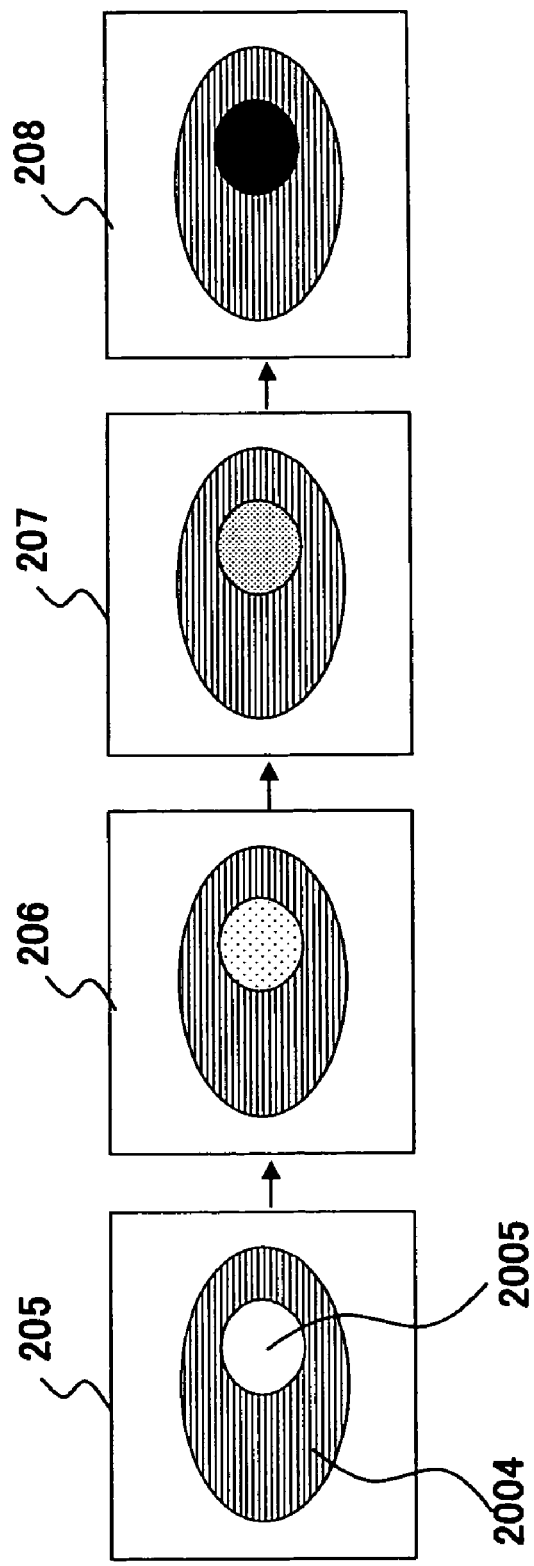
FIG. 11(b) is a schematic diagram to show an example of a cineangiogram in which the concentration value of a contrast medium injected into the object changes time dependently.

The images 201 to the image 204 of FIG. 11(a) and FIG. 11(b) are cineangiograms, and the time elapses in order of 201 to 204. Similarly, the images 205 to 208 are cineangiograms, and the time elapses in order of 205 to 208. Reference numeral 2001 denotes a region 1, reference numeral 2002 denotes a region 2, reference numeral 2003 denotes a region 3, reference numeral 2004 denotes a region 1, and reference numeral 2005 denotes a region 2, respectively.

FIG. 11(a) and FIG. 11(b) show a process to obtain an average value of pixel values from time t to time t+Δt with respect to a region where the amount of change obtained as a difference between a pixel value at a time t and a pixel value at a time t+Δt of the image data with three or more dimensional coordinates including a time coordinate according to the present invention is below a predetermined threshold value. FIG. 11(a) illustrates an example in which a pixel value changes time dependently depending the movement of an object, and includes the region 2001 where there is no change of a pixel value (smaller than a threshold value) due to the movement of an object from the image 201 to the image 204, the region 2002 where a pixel value changes due to the movement of the object, and the region 2003 (the threshold value T and more). In this case, the application of a sum average filter along the time axis or a filtering process along the time axis to the region 2001 to reduce noise makes it possible to reduce noise across the whole image without giving any influence on the movement.

The pixel value may be associated with at least one of a chromaticity value, a color density value, and a lightness value.

FIG. 11(b) shows an example in which the concentration value due to a contrast medium injected into a target object changes time dependently. The images 205 to 208 include the region 2004 where there is no change of the concentration value due to a contrast medium (smaller than a threshold value), the region 2005 where a concentration value changes due to a contrast medium (the threshold value T and more). In this case, the application of a sum average filter along the time axis or a filtering process along the time axis to the region 2004 for noise reduction makes it possible to reduce noise across the whole image without giving any influence on the change of concentration value due to a contrast medium (spread of a contrast medium). In this case also, the pixel value may be associated with at least one of a chromaticity value, a color density value, and a lightness value.

Therefore, it is assumed that if the amount of change of a pixel value in data which change along the time axis is small, it is a noise element (fluctuation) rather than the moving element in the amount of change that causes the change.

Application of a sum average filter along the time axis or a filtering along the time axis for noise reduction (smoothing) to the region where the moving element is small provides an image from which the noise element is dominantly excluded along the time axis.

However, if there is a concentration fluctuation due to a contrast medium, the region with the concentration fluctuation shows a high pixel value signal, which usually makes the influence of noise negligible. Thus the influence of noise is not a problem. But since noise can be reduced further in a region where the influence of noise is already small, an almost perfect image is acquired.

EXAMPLE 6

FIG. 12 is a flow chart to show a procedure (algorithm) to extract a contrasted blood vessel and a contrasted organ according to the present invention.

Now, the procedure will be explained along with each step of FIG. 12 below.

First, at step S1201 the procedure is started.

At step S1202, a maximum value pixel MXI (X,Y,Z) which shows the maximum value along the time axis is extracted along the time axis at each pixel coordinate position in image data in which the pixel value of each pixel changes time dependently. The maximum value pixel has a pixel value at a time phase when the effect of a contrast medium is the highest. Then at step S1203, a minimum value pixel MNI (X,Y,Z) which shows the minimum value along the time axis is extracted to the image data along the time axis. Alternatively, a smaller value pixel after a filtering process along the time axis is extracted along the time axis. The smaller value pixel has a pixel value corresponding to the one at a time phase when the effect of a contrast medium is the lowest.

The maximum value pixel MXI (X,Y,Z) and the minimum value pixel MNI (X,Y,Z) can be obtained by a method such as that described in the first embodiment.

At step S1204, by differencing using the difference between the two pixel values MXI (X,Y,Z)−MNI (X,Y,Z), a contrasted blood vessel can be obtained. If priority is given to the processing speed in this step, a difference is desirably performed after the maximum value pixel and the minimum value pixel are extracted, but this tends to increase a noise amount when a difference is performed on images which have noise.

So, when priority is given to a high quality in view of noise, a difference is preferably performed for an image which is extracted by a filtering process along the time axis and has a relatively large pixel value and an image which is extracted by a filtering process along the time axis and has a relatively small pixel value.

If noise is extracted when a contrasted blood vessel is extracted along the time axis by a filtering process along the time axis and this causes a problem, the noise element is reduced or removed by a threshold process or a filtering process along the time axis after a difference is performed.

A maximum value image with noise removed may be generated by applying a filter along the time axis to extract a maximum pixel value along the time axis for each pixel coordinate position in image data arranged in time series and a filter along the time axis to remove noise along the time axis. Similarly, a minimum value image with noise removed may be generated by applying a filter along the time axis to extract a minimum pixel value along the time axis for each pixel coordinate position in image data arranged in time series and a filter along the time axis to remove noise along the time axis.

Then a difference is performed on the maximum value image and the minimum value image to produce a difference image.

Moreover, the use of a window function along the time axis makes it possible to separate artery from vein.

EXAMPLE 7

Figure 13:
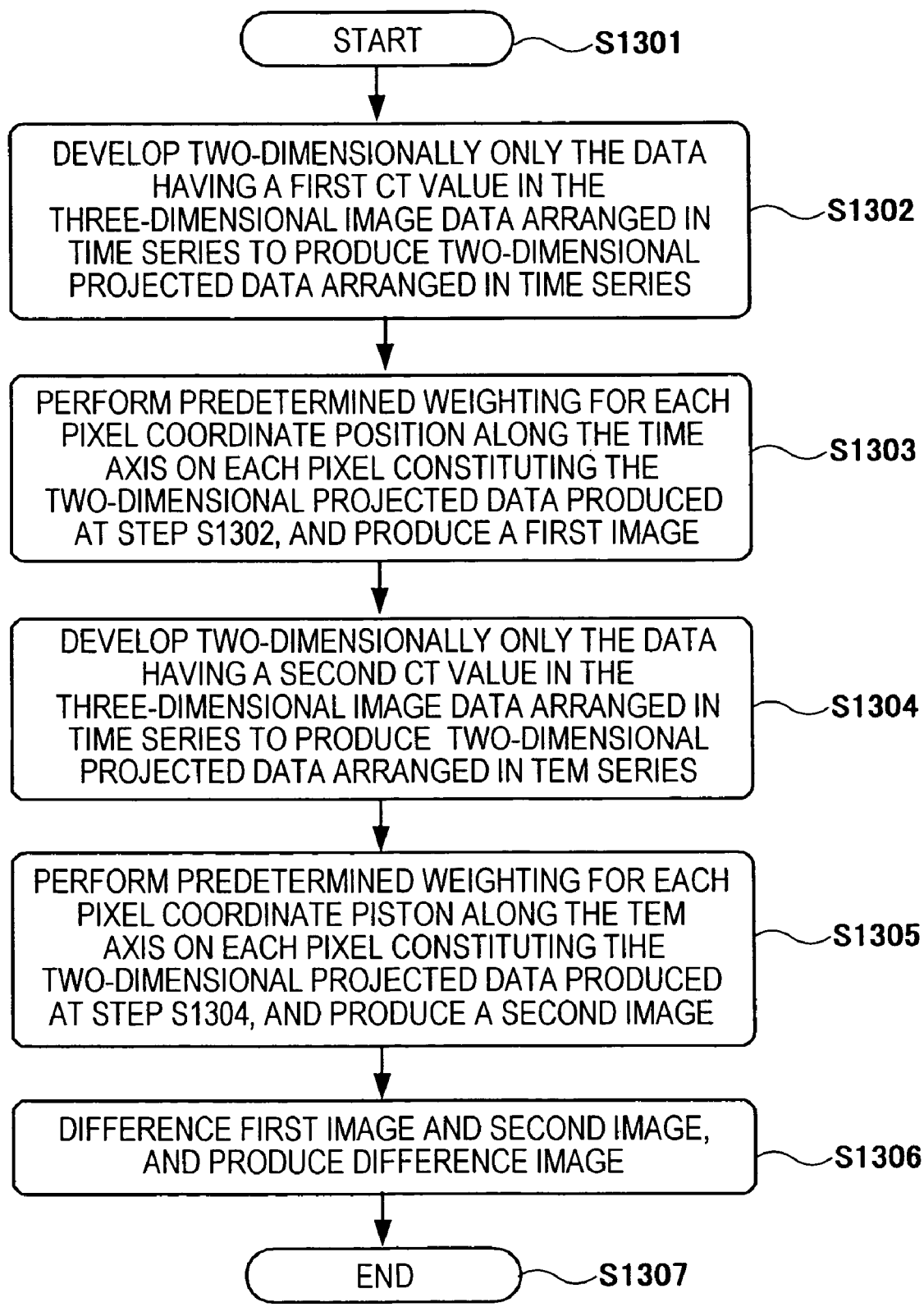
FIG. 13 is a flow chart to show a process to produce a difference image of one embodiment according to the present invention, and shows an example to produce a difference image from a difference between a plurality of images produced by performing a filtering process along the time axis process on two-dimensional projected image data generated with an MIP method.

Referring to FIG. 13, a method to difference a plurality of two-dimensional projected image data generated by MIP (Maximun Intensity Projection) will be explained. FIG. 13 is a schematic diagram to show a process to produce a difference image of one embodiment according to the present invention, and is a flow chart to show an example to produce a difference image by differencing a plurality of images produced by applying a filtering process along the time axis process to two-dimensional projected image data generated by an MIP method.

Now, the process will be explained along with each step of FIG. 13 below.

First, at step S1301 the processing is started.

At step S1302, only the data corresponding to a first CT value, for example the lowest CT value, which is contained in the image data (slice data) taken by the X-ray CT apparatus 1 or the MRI apparatus 4 and arranged in time series is developed two-dimensionally to generate two-dimensional projected data arranged in time series.

At step S1303, a filtering process is performed for each pixel coordinate position along the time axis on each pixel constituting the two-dimensional projected data produced at step S1302 and arranged in time series to perform a predetermined weighting along the time axis along the time series. A first image is produced based on the image data after the weighting along the time axis.

At step S1304, only the data corresponding to a second CT value, for example the highest CT value, which is contained in the image data (slice data) arranged in time series is developed two-dimensionally to generate two-dimensional projected data arranged in time series.

At step S1305, a filtering process is performed for each pixel coordinate position along the time axis on each pixel constituting the two-dimensional projected data produced at step S1304 and arranged in time series to perform a predetermined weighting along the time axis along the time series. A second image is produced based on the image data after the weighting along the time axis.

At step S1307, the process is completed.

At step S1306, a difference image is generated between a first image and a second image. This provides a high quality image in view of noise, by extracting an image which is extracted by a filtering process along the time axis and has a relatively large pixel value and an image which is extracted by a filtering process along the time axis and has a relatively small pixel value and performing a difference on the images.

A filter along the time axis for noise reduction may be applied to the two-dimensional projected data after the weighting along the time axis to generate a first image and a second image.

From the above description about various examples of the present invention, the objects of the present invention are apparently achieved. Several embodiments have been described and illustrated in detail in connection with the present invention, but the description is for the purpose of illustration only, and the invention is not limited to these embodiments. Moreover, the present invention is not limited to the purpose for imaging a contrasted blood vessel, but may be applied to an image which includes a region where the pixel value of a pixel changes time dependently with various purposes such as an evaluation of the spread of a contrast medium into tissues.

In the above Examples, a three-dimensional image is reconstructed based on image data taken by the X-ray CT apparatus 1 or the MRI apparatus 4, and an image processing is performed on a region of interest in the three-dimensional image. However, an image processing may be performed similarly on the whole region of the image set by the image data without setting a region of interest.

The above Examples are explained with the use of the X-ray CT apparatus 1 and the MRI apparatus 4, but the other medical imaging apparatuses which provide image data on a subject, for example, a PET apparatus, a SPECT apparatus, a CT apparatus using positron or gamma ray such as a gamma camera, a CT apparatus using neutral ray or light, ultrasonic wave diagnosis apparatus, a DSA apparatus, and an X-ray equipment may be used.

Figure 14:
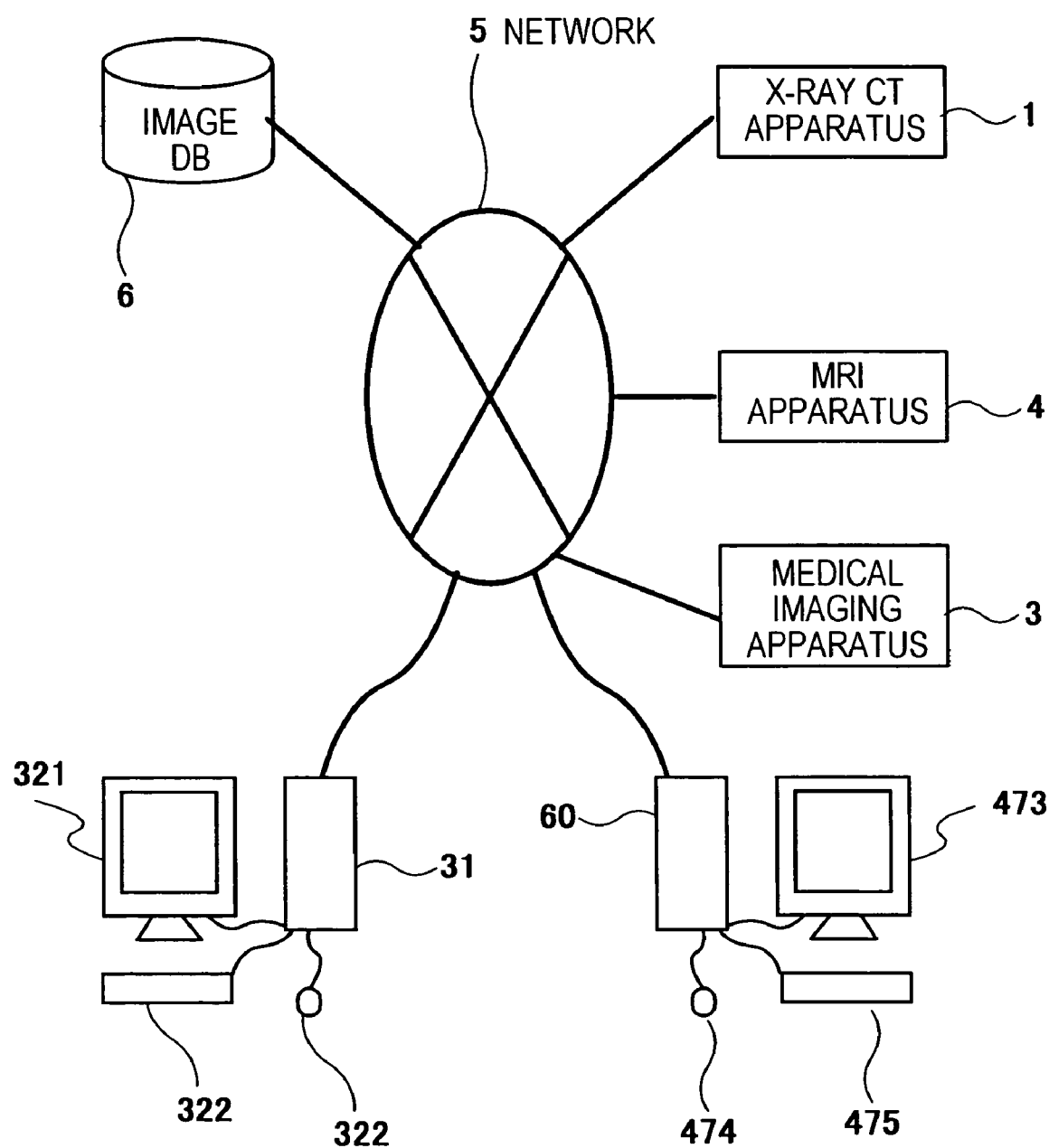
FIG. 14 is an entire structural diagram to show a computer aided detection of one embodiment according to the present invention.

In the above Examples, the X-ray CT apparatus 1 and the MRI apparatus 4 perform an image processing with the operation device 31 and the CPU 48 placed in the processing unit 30 and the processing unit 60 connected via a power source/signal line 33 and a power source/signal line 70. However, for example as shown in FIG. 14, the present invention may be applied to a computer aided detection in which the X-ray CT apparatus 1, the MRI apparatus 4, or other medical imaging apparatus 3 are connected to an image processing device, for example an operation device 31 and a processing unit 60, via a network 5. In this case, the image data taken by the X-ray CT apparatus 1, the MRI apparatus 4, or other medical imaging apparatus 3 is input into the image processing device, for example the operation device 31 and the processing unit 60, via the network 5. Then the image processing devices, for example the operation device 31 and the processing unit 60 perform an image processing according to the present invention based on the input image data.

The image data taken by the X-ray CT apparatus 1, the MRI apparatus 4, or other medical imaging apparatus 3 may be stored in an image database (image DB) 6 which is connected to a network 5 to store image data. An image processing device may obtain image data from the image DB 6 to perform an image processing based on the image data obtained from the image DB 6.

An image processing device also may perform an image processing similar to the above Examples based on the image data which is read out from a memory device connected to the image processing device such as an FDD, a hard disc drive, a CD-ROM drive, an optical magnetic disc (MO) drive, a ZIP drive, a PD drive, and a DVD drive.

Each embodiment shown in this embodiment is used as a single unit, but may be used as a combination, which is particularly highly effective.

INDUSTRIAL APPLICABILITY

As described above, according to the present invention, the present invention may be applied to an application to display a desired image, for example an image with noise reduced along the time axis and a three-dimensional spatial image of a contrasted blood vessel, based on image data which are taken by a medical imaging apparatus in time series. The present invention also may be applied to an application to extract a certain region from image data.

The invention claimed is:

1. An image processing method, comprising:
   an inputting step of inputting an image data which is obtained by imaging a subject for a predetermined period of time with a medical imaging apparatus and is arranged in time series;
   an extracting along a time axis step of extracting pixels which satisfy a predetermined condition along a time axis from all the pixels arranged in time series for each pixel coordinate position with respect to each pixel in the image data; and
   a constructing step of constructing a two-dimensional or three-dimensional image based on the pixels extracted along the time axis in the extracting along the time axis step, wherein
   the extracting along the time axis step comprises: a first extracting along the time axis step of extracting a pixel having a first characteristic from all the pixels arranged in time series for each pixel coordinate position along the time axis; and a second extracting along the time axis step of extracting a pixel having a second characteristic from all the pixels arranged in time series along the time axis, and
   the constructing step comprises: a first constructing step of constructing a first image based on the pixel having the first characteristic; and a second constructing step of constructing a second image based on the pixel having the second characteristic, and
   the image processing method further comprises: a difference operation step of performing a difference operation on the first image and the second image; and a difference image producing step of producing a difference image based on the result of the difference operation.

2. The image processing method according to claim 1, further comprising:
   an image reconstructing step of reconstructing a two-dimensional or three-dimensional image which corresponds to a two-dimensional or three-dimensional range of the subject based on the image data; and
   a region of interest setting step of setting at least one region of interest for the two-dimensional or three-dimensional image,
   wherein the extracting along the time axis step comprises extracting pixels which satisfy a predetermined condition along the time axis from all the pixels arranged in time series for each pixel coordinate position for each pixel constituting the region of interest.

3. The image processing method according to claim 1, wherein the predetermined condition is to extract a pixel having a maximum pixel value along the time axis from all the pixels arranged in time series at each pixel coordinate position.

4. The image processing method according to claim 1, wherein the predetermined condition is to extract a pixel having an arbitrary pixel value among pixel values corresponding to each pixel arranged in time series at each pixel coordinate position along the time axis.

5. The image processing method according to claim 1, wherein the extracting along the time axis step comprises: sequentially comparing a pixel value at a first time in the predetermined period of time with a pixel value at a second time in the predetermined period of time for each pixel coordinate position with respect to each pixel in the image data along the time series; and extracting pixels which satisfy a predetermined condition along the time axis.

6. The image processing method according to claim 1, wherein the extracting along the time axis step comprises: a filtering process along the time axis to perform a predetermined filtering process on all the pixels arranged in time series for each pixel coordinate position along the time axis and obtain pixels representing each pixel coordinate position.

7. An image processing method comprising:
- an inputting step of inputting an image data which is obtained by imaging a subject for a predetermined period of time with a medical imaging apparatus and is arranged in time series;
- an extracting along a time axis step of extracting pixels which satisfy a predetermined condition along a time axis from all the pixels arranged in time series for each pixel coordinate position with respect to each pixel in the image data; and
- a constructing step of constructing a two-dimensional or three-dimensional image based on the pixels extracted along the time axis in the extracting along the time axis step, wherein
- the extracting along the time axis step comprises: a first extracting along the time axis step of extracting a pixel having a first characteristic from all the pixels arranged in time series for each pixel coordinate position along the time axis; and a second extracting along the time axis step of extracting a pixel having a second characteristic from all the pixels arranged in time series along the time axis, and
- the constructing step comprises: a first constructing step of constructing a first image based on the pixel having the first characteristic; and a second constructing step of constructing a second image based on the pixel having the second characteristic, and
- the image processing method further comprises: a difference operation step of performing a difference operation on the first image and the second image; and a difference image producing step of producing a difference image based on the result of the difference operation,
- wherein the pixel having the first characteristic is the maximum pixel value in the pixel values of all the pixels arranged in time series at each pixel coordinate position, and the pixel having the second characteristic is the minimum pixel value in the pixel values of all the pixels arranged in time series at each pixel coordinate position.

8. The image processing method according to claim 7, further comprising:
- an image reconstructing step of reconstructing a two-dimensional or three-dimensional image which corresponds to a two-dimensional or three-dimensional range of the subject based on the image data; and
- a region of interest setting step of setting at least one region of interest for the two-dimensional or three-dimensional image,
- wherein the extracting along the time axis step comprises extracting pixels which satisfy a predetermined condition along the time axis from all the pixels arranged in time series for each pixel coordinate position for each pixel constituting the region of interest.

9. The image processing method according to claim 7, wherein the predetermined condition is to extract a pixel having a maximum pixel value along the time axis from all the pixels arranged in time series at each pixel coordinate position.

10. The image processing method according to claim 7, wherein the predetermined condition is to extract a pixel having an arbitrary pixel value among pixel values corresponding to each pixel arranged in time series at each pixel coordinate position along the time axis.

11. The image processing method according to claim 7, wherein the extracting along the time axis step comprises: sequentially comparing a pixel value at a first time in the predetermined period of time with a pixel value at a second time in the predetermined period of time for each pixel coordinate position with respect to each pixel in the image data along the time series; and extracting pixels which satisfy a predetermined condition along the time axis.

12. The image processing method according to claim 7, wherein the extracting along the time axis step comprises: a filtering process along the time axis to perform a predetermined filtering process on all the pixels arranged in time series for each pixel coordinate position along the time axis and obtain pixels representing each pixel coordinate position.

13. An image processing method, comprising:
- an inputting step of inputting an image data obtained by imaging a subject into which a contrast medium is injected for a predetermined period of time with a medical imaging apparatus and arranged in time series;
- an image reconstructing step of reconstructing three-dimensional images arranged in time series based on the image data;
- an extracting along the time axis step of extracting a maximum value pixel which has a clearest contrasted image by the contrast medium and a minimum value pixel which has little or no residual contrast medium therein from all the pixels arranged in time series for each pixel coordinate position along the time axis with respect to each pixel constituting the three-dimensional images arranged in time series;
- a constructing step of constructing a two-dimensional or three-dimensional image which has a clearest contrasted image by the contrast medium based on the maximum value pixel and a two-dimensional or three-dimensional image with no or little residual contrast medium therein based on the minimum value pixel;
- a difference operation step of performing a difference operation on the two-dimensional or three-dimensional image which has a clearest contrasted image by the contrast medium and the two-dimensional or three-dimensional image with no or little residual contrast medium therein; and
- a difference image producing step of producing a difference image based on the result of the difference operation.

14. An image processing device, comprising:
- an input means which inputs an image data obtained by imaging a subject into which a contrast medium is injected for a predetermined period of time with a medical imaging apparatus and arranged in time series;
- an image reconstructing means reconstructs three-dimensional images arranged in time series based on the image data;
- an extracting along the time axis means which extracts a maximum value pixel which has a clearest contrasted image by the contrast medium and a minimum value pixel which has little or no residual contrast medium therein from all the pixels arranged in time series for each pixel coordinate position along the time axis with respect to each pixel constituting the three-dimensional images arranged in time series;
- a construction means which constructs a two-dimensional or three-dimensional image which has a clearest contrasted image by the contrast medium based on the maximum value pixel and a two-dimensional or three-dimensional image with no or little residual contrast medium therein based on the minimum value pixel;

a difference operation means which performs a difference operation on the two-dimensional or three-dimensional image which has a clearest contrasted image by the contrast medium and the two-dimensional or three-dimensional image with no or little residual contrast medium therein; and a difference image producing means which produces a difference image based on the result of the difference operation.

15. A computer aided detection, comprising:

a medical imaging apparatus which obtains an image data arranged in time series by imaging a subject for a predetermined period of time;

an operation device which constructs a two-dimensional or three-dimensional image based on the image data; and a displaying device which displays an image produced by the operation device, wherein the operation device comprises:

an input means which inputs the image data obtained by imaging a subject into which a contrast medium is injected for a predetermined period of time with a medical imaging apparatus and arranged in time series;

an image reconstructing means which reconstructs three-dimensional images arranged in time series based on the mage data;

an extracting along the time axis means which extracts a maximum value pixel which has a clearest contrasted image by the contrast medium and a minimum value pixel which has little or no residual contrast medium therein from all the pixels arranged in time series for each pixel coordinate position along the time axis with respect o each pixel constituting the three-dimensional images arranged in time series;

a constructing means which constructs a two-dimensional or three-dimensional image which has a clearest contrasted image by the contrast medium based on the maximum value pixel and a two-dimensional or three-dimensional image with no or little residual contrast medium therein based on the minimum value pixel;

a difference operation means which performs a difference operation on the two-dimensional or three-dimensional image which has a clearest contrasted image by the contrast medium and the two-dimensional or three-dimensional image with no or little residual contrast medium therein; and a difference image producing means which produces a difference image based on the result of the difference operation, and wherein the displaying device displays the difference image produced by the difference image producing means.

* * * * *